US012757907B1

(12) United States Patent
Balakrishnan

(10) Patent No.: US 12,757,907 B1
(45) Date of Patent: Oct. 13, 2026

(54) FOOD DEHYDRATION DEVICE

(71) Applicant: PRINCE MOHAMMAD BIN FAHD UNIVERSITY, Dhahran (SA)

(72) Inventor: Deepanraj Balakrishnan, Dhahran (SA)

(73) Assignee: PRINCE MOHAMMAD BIN FAHD UNIVERSITY, Dhahran (SA)

( * ) Notice: Subject to any disclaimer, the term of this patent is extended or adjusted under 35 U.S.C. 154(b) by 0 days.

(21) Appl. No.: 19/549,168

(22) Filed: Feb. 25, 2026

(51) Int. Cl.

| | |
|---|---|
| ***A23B 2/97*** | (2025.01) |
| ***A23B 2/00*** | (2025.01) |
| ***A23B 2/53*** | (2025.01) |
| ***A61L 2/104*** | (2026.01) |
| ***A61L 2/24*** | (2006.01) |
| ***G05D 7/06*** | (2006.01) |

(52) U.S. Cl.

CPC ................ *A23B 2/97* (2025.01); *A23B 2/001* (2025.01); *A23B 2/003* (2025.01); *A23B 2/53* (2025.01); *A61L 2/104* (2026.01); *A61L 2/24* (2013.01); *G05D 7/0676* (2013.01); *A61L 2202/11* (2013.01); *A61L 2202/14* (2013.01)

(58) Field of Classification Search

CPC .. A23B 2/97; A23B 2/001; A23B 2/53; A61L 2/104; A61L 2/24; A61L 2202/11; A61L 2202/14

USPC ........................................................... 34/275

See application file for complete search history.

(56) References Cited

FOREIGN PATENT DOCUMENTS

| | | | |
|---|---|---|---|
| CN | 103994652 | A | 8/2014 |
| CN | 223388840 | U | 9/2025 |
| IN | 202521074697 | | 8/2025 |
| KR | 10-2018-0003343 | A | 1/2018 |

OTHER PUBLICATIONS

Maximiliano Martín Del Campo, et al., "Validation of a hybrid solar-electrical dryer through computational fluid dynamics simulation and practical approach applied to the Kent mango variety", Smart Agricultural Technology, vol. 10, Mar. 2025, 100836, 11 Pages.

*Primary Examiner* — Connor J Tremarche

(74) *Attorney, Agent, or Firm* — Oblon, McClelland, Maier & Neustadt, L.L.P.

(57) ABSTRACT

A food dehydration device includes a dehydrating cabinet with chambers. Each chamber includes an inlet port, an outlet port, a removable partition, and an adjustable tray. A sensing array includes a humidity sensor positioned at both the inlet and outlet ports. A temperature sensor is positioned on the tray, and an airflow sensor is positioned in the upper region of a sidewall of the chambers. A dehydrating unit disposed in the chambers includes a thermal unit, a pulsed electric field unit, and an ultrasound-assisted dehydrating unit. An ultraviolet-C lamp is disposed in the chambers, and a safety interlock mechanism. An airflow management unit includes a variable-speed fan and an exhaust vent. An energy module includes a solar thermal collector and an electric heating element. A microcontroller to compute power output and a cloud-based communication module to transmit performance data.

20 Claims, 14 Drawing Sheets

FOOD DEHYDRATION DEVICE

BACKGROUND

Technical Field

The present disclosure is directed to a food processing and preservation system, and more particularly, to a food dehydration device.

Description of Related Art

The "background" description provided herein is for the purpose of presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Food dehydration is widely used to extend shelf life, reduce transportation weight, and preserve nutritional and sensory attributes of food products. Conventional dehydration systems typically use convective hot-air drying, which removes moisture by exposing food to elevated temperatures for extended periods. While such approaches are commonly used in domestic, commercial, and industrial settings, they may lead to non-uniform drying conditions, prolonged processing times, and degradation of heat-sensitive nutrients, texture, or color.

In some existing dehydration devices, airflow and temperature are applied uniformly across a drying chamber without accounting for localized variations in moisture content, airflow distribution, or loading conditions. As a result, food products positioned at different locations within the device may experience inconsistent dehydration rates, leading to uneven moisture removal and variability in product quality. To improve uniformity, multi-tray configurations and fixed airflow paths are introduced in dehydrating devices; however, they are limited in their ability to adapt dynamically to changing dehydration conditions.

Various technologies have been explored to enhance dehydration efficiency or microbial safety. For example, pulsed electric field (PEF) treatment, ultrasound-assisted processing, and ultraviolet (UV) irradiation have been investigated individually in food processing applications. These technologies are often implemented as standalone systems or as add-on modules, and their integration into dehydration devices may raise challenges related to safety, control coordination, energy management, and process optimization. Ensuring safe operation when high-voltage, acoustic, or ultraviolet components are present may require additional safeguards.

Additionally, energy consumption remains a significant consideration in dehydration processes. Conventional electric heating systems may be energy-intensive, especially when operated continuously or at elevated temperatures. Alternative energy sources, such as solar-based heating, have been proposed to reduce energy demand. However, integrating such sources into controlled-dehydration environments while maintaining consistent operating conditions may pose technical challenges.

Sensor technologies capable of measuring parameters such as temperature, humidity, and airflow are known in the art. In many dehydration systems, however, sensor placement, environmental protection, and resolution may limit their ability to accurately characterize localized conditions within a drying environment. Without reliable sensing and feedback, it may be difficult to dynamically adjust operating parameters to attain uniform, repeatable dehydration results.

CN223388840U describes drying equipment used in pet food processing. The drying equipment includes a drying cabinet shell. A heating chamber is arranged at the bottom of the drying cabinet shell, a plurality of pipeline chambers are arranged above the heating chamber, a drying chamber is arranged between two adjacent pipeline chambers, a vertical pipeline mounting groove is formed in the left side of the drying chamber, a heating block is arranged in the heating chamber, a blower matched with the heating block is arranged in the pipeline chamber at the bottom, and a pipeline assembly is connected to the blower.

CN103994652A describes thin-layer drying experimental equipment and drying technology thereof. The equipment includes a constant-temperature, constant-humidity chamber, a fan, manual-control dampers, a heater, a hot-air pipeline, wind-speed sensors, temperature and humidity sensors, and valves. The constant-temperature and humidity machine is installed at the air inlet position of the entire experimental equipment. The fan is linked to the constant-temperature and humidity machine. The manual control dampers are arranged between the constant temperature and humidity machine and the air suction opening of the fan. The heater is connected to the air outlet of the fan in a linkage mode through a pipeline. The hot air pipeline is routed from the heater's air outlet and connected to the two ends of the drying chamber via two branches in a linkage mode. The wind speed sensors, the temperature and humidity sensors, and the valves are arranged on the hot air pipeline.

Each of the aforementioned conventional food dehydration devices has one or more drawbacks that hinder adoption, including limited control over dehydration conditions, non-uniform moisture removal across food products, and inefficient energy use, which may adversely affect processing efficiency and product quality. Accordingly, one object of the present disclosure is to provide a food dehydration device that enhances process efficiency and flexibility across thermal and non-thermal treatment technologies, while maintaining operational safety and energy efficiency.

SUMMARY

In an exemplary embodiment, a food dehydration device is described. The food dehydration device includes a dehydrating cabinet including a plurality of chambers. Each chamber includes an inlet port, an outlet port, a removable partition, and an adjustable tray. The chambers are thermally isolated from one another by the removable partition selected from the group consisting of an aerogel-based insulation panel, a vacuum-insulated panel (VIP), a ceramic-fiber insulation panel, and a silica-based microporous insulation panel. A sensing array is disposed within each chamber. The sensing array includes a humidity sensor positioned at the inlet port and the outlet port and is configured to measure a relative humidity gradient. A temperature sensor is positioned at the tray and is configured to detect a chamber temperature, and an airflow sensor is positioned at an upper region of a sidewall of the chambers and is configured to measure airflow velocity. A dehydrating unit is disposed in the chambers, which includes a thermal unit configured to deliver heat energy. The dehydrating unit further includes a pulsed electric field (PEF) unit configured to deliver high-voltage pulses and an ultrasound-assisted dehydrating (UAD) unit configured to generate acoustic waves. An ultraviolet-C (UV-C) lamp is disposed in the chambers and is configured to activate during low-temperature dehydrating cycles. A safety interlock mechanism is configured to deactivate the UV-C lamp, the PEF unit, and the (UAD) unit when a corresponding chamber is open. An airflow management unit includes a variable-speed fan disposed at the inlet port and the outlet port configured to drive air through the chambers. The airflow management unit further includes an exhaust vent disposed at the outlet port, including actuators configured to regulate an exhaust flow path. The airflow management unit is configured to modulate airflow based on the relative humidity gradient between the inlet port and the outlet port and adjust a fan speed and a vent aperture to maintain a uniform dehydrating condition across the chambers. An energy module is disposed at a surface of the cabinet. The energy module includes a solar thermal collector and an electric heating element, a microcontroller operatively coupled to the energy module, the sensing array, the UV-C lamp, the dehydrating unit, and the airflow management unit. The microcontroller is configured to compute a power output to the dehydrating unit and the airflow management unit, calculate a moisture content of a food load and dynamically adjust the relative humidity gradient, the chamber temperature, and the relative humidity within the chambers and a cloud-based communication module configured to transmit performance data and system alerts to a remote display interface and transmit an external input to the microcontroller.

In some embodiments, the cabinet is constructed from a corrosion-resistant material selected from the group consisting of stainless steel, aluminum alloy, and a polymer-metal composition. The dehydrating cabinet includes one or more walls having a thickness between about 1.0 and 4.0 mm. The dehydrating cabinet has an overall internal volume between about 50 and 500 liters, and each chamber within the dehydrating cabinet has a width between about 150 and 600 mm, a depth between about 200 and 800 mm, and a height between about 150 and 700 mm.

In some embodiments, the sensing array includes a first humidity sensor positioned about 5 to 20 mm from the inlet port, a second humidity sensor positioned about 5 to 20 mm from the outlet port, the temperature sensor disposed at the tray about 5 to 30 mm from the sidewall of the chambers, the airflow sensor disposed at the sidewall of the chambers, about 20 to 50 mm from a surface level of the tray. Each sensor is encapsulated in a polymer coating selected from the group consisting of a parylene-C conformal coating, a silicone-based encapsulant, and a fluoropolymer coating.

In some embodiments, the humidity sensor includes a polymer-film humidity sensor selected from the group consisting of a polyimide-based capacitive humidity sensor, a polyethylene-terephthalate (PET)-based capacitive humidity sensor, a polyvinyl-alcohol (PVA)-based capacitive humidity sensor, a cellulose-acetate-based capacitive humidity sensor, and a fluoropolymer-based capacitive humidity sensor. The humidity sensor has a sensing area of about 4 to 25 $mm^2$.

In some embodiments, the temperature sensor includes a thin-film resistive temperature detector (RTD) selected from the group consisting of a platinum thin-film RTD, a nickel thin-film RTD, a copper thin-film RTD, a graphene-based thermoresistive temperature sensor, and an MXene-based thermoresistive temperature sensor. The temperature sensor has a sensing area between 3 and 20 $mm^2$.

In some embodiments, the airflow sensor is selected from the group consisting of a thermal anemometric airflow sensor, a MEMS-based airflow sensor, a hot-wire airflow sensor, a piezoresistive differential pressure airflow sensor, and an ultrasonic time-of-flight airflow sensor. The airflow sensor has a sensing area between about 3 and 20 $mm^2$.

In some embodiments, the thermal unit includes a convective heating element selected from the group consisting of an electrical resistance heating coil, a ceramic heating element, a finned tubular heater, and a radiant-convective hybrid heater. The thermal unit is configured to deliver the heat energy to the chambers via a forced airflow generated by the variable-speed fan at the airflow velocity of about 0.5 to 5.0 m/s, operate at the power output between 300 and 1500 W, attain a thermal response time sufficient to raise the chamber temperature from 25° C. to 60° C. within about 2 minutes to 6 minutes and maintain the chamber temperature at about 40° C. to 80° C. during dehydration.

In some embodiments, the PEF unit includes parallel-plate electrodes spaced between 5 and 25 mm apart and operates at a repetition rate between 10 and 500 Hz. The PEF unit includes a high-voltage pulse generator selected from the group consisting of a capacitor-discharge pulse generator, a Marx-bank pulse generator, and a solid-state insulated-gate bipolar transistor (IGBT) pulse generator. The PEF unit is configured to generate the high-voltage pulses having a field strength between 0.5 and 5 kV/cm and a pulse width between 1 and 50 μs.

In some embodiments, the UAD unit includes at least one ultrasonic transducer disposed on the sidewall of the chambers. The ultrasonic transducer is selected from the group consisting of a piezoelectric ceramic transducer, a piezoelectric composite transducer, a magnetostrictive transducer, and a thin-film MEMS ultrasonic transducer. The ultrasonic transducer operates at about 20 to 60 kHz and at a duty cycle of about 20 to 80%.

In some embodiments, the UV-C lamp includes at least one emitter selected from the group consisting of a low-pressure mercury vapor emitter, a pulsed xenon excimer emitter, a krypton-chloride excimer emitter, a UV-C light-emitting diode (LED) emitter, and a plasma-discharge emitter. The UV-C lamp emits radiation between 200 and 280 nm and has an irradiance output between 0.5 and 3.0 $mW/cm^2$.

In some embodiments, the safety interlock mechanism includes at least one selected from the group consisting of a magnetic reed switch, a mechanical microswitch, an optical proximity sensor, and a Hall-effect sensor.

In some embodiments, the variable-speed fan includes a brushless DC (BLDC) motor actuator selected from the group consisting of a sensorless BLDC actuator, a Hall-sensor-based BLDC actuator, a PWM-driven BLDC actuator, and a closed-loop BLDC actuator. The variable-speed fan is configured to generate airflow velocities between 0.5 m/s and 5.0 m/s and to maintain a static pressure between 20 and 120 Pa.

In some embodiments, the exhaust vent includes a stepper motor-driven actuator selected from the group consisting of a bipolar stepper motor, a unipolar stepper motor, a micro-stepping stepper motor, a permanent magnet stepper actuator, and a variable reluctance stepper actuator. The exhaust vent is configured to modulate the vent aperture between 5% and 95% open, regulate exhaust flow rate about 0.1 to 1.5 $m^3$/min, and maintain a pressure-balanced airflow across the chambers.

In some embodiments, the solar thermal collector is selected from the group consisting of a flat-plate solar thermal collector, an evacuated-tube solar collector, and a compound parabolic concentrator. The solar thermal collector is configured to provide supplemental heating when solar irradiance exceeds 300 $W/m^2$. The solar thermal collector is thermally coupled to the cabinet to heat the chambers through a convective heat-exchange interface, including at least one of a direct air-loop coupling and a closed-loop thermal-fluid circuit. The thermal fluid circuit operates at a flow rate of about 0.2 to 1.5 L/min.

In some embodiments, the microcontroller includes a multivariable proportional-integral-derivative (PID) control model configured to compute the power output u (t) according to a mathematical expression (1):

$$u(t) = K_p e(t) + K_i \int_0^t e(\tau)\, d\tau + K_d \frac{de(t)}{dt} \tag{1}$$

where $$e(t) = \begin{bmatrix} e_H(t) \\ e_T(t) \end{bmatrix}$$

represents humidity and temperature error vectors, $$u(t) = \begin{bmatrix} u_F(t) \\ u_V(t) \end{bmatrix}$$

represents the power output applied to the thermal unit and the airflow management unit, $K_p$ is a proportional gain matrix of about 0.5 and 3.0, $K_i$ is an integral gain matrix of about 0.01 $s^{-1}$ to 0.50 $s^{-1}$, $K_d$ is a derivative gain matrix of about 0.001 s to 0.10 s.

In some embodiments, the microcontroller is configured to control activation of the thermal unit, the PEF unit, and the UAD unit according to an activation sequence defined by Equation (2):

$$S(t) = \begin{cases} \text{Thermal}, & \text{if } \frac{dH}{dt} < \alpha \\ PEF, & \text{if } \frac{dH}{dt} \geq \alpha \text{ and } \Delta T < \beta \\ UAD, & \text{if } H \leq \gamma \end{cases} \tag{2}$$

Where S(t) represents a mode-selection vector defining activation of the thermal unit, the PEF unit, and the UAD unit, $$\frac{dH}{dt}$$

is a humidity rate of change, ΔT is a temperature deviation, H is the relative humidity within the chambers, α is a humidity rate-of-change threshold between about 0.5 and 2.0% RH/min, β is a temperature-deviation threshold between about 1° C. and 3° C., and γ is a chamber-humidity threshold between about 5% RH and 20% RH.

The microcontroller is configured to transition the activation sequence, including from the thermal unit to the PEF unit when the humidity rate of change exceeds the humidity rate-of-change threshold, and from the PEF unit to the UAD unit when the temperature deviation is below the temperature-deviation threshold, and from the UAD unit to a termination state when the relative humidity is below the chamber-humidity threshold.

In some embodiments, the microcontroller is further configured to apply a multi-condition gating to the activation sequence including initiating the thermal unit to raise the chamber temperature between 40° C. and 80° C., initiating the PEF unit when the humidity rate of change exceeds a humidity-rate-of-change threshold between 0.5 and 2.0% RH/min, and the chamber temperature is between 35° C. and 50° C., initiating the UAD unit when the temperature deviation remains within the temperature-deviation threshold between 1° C. and 3° C., and the relative humidity gradient between the inlet and outlet ports is about 3% RH to 15% RH. Maintaining the UAD unit while the relative humidity decreases at a rate between 0.2 and 1.0% RH/min, and the airflow velocity remains between 0.5 m/s and 3.0 m/s. Terminating the activation sequence when either the relative humidity is below a termination threshold between 5% RH and 15% RH, or the humidity rate of change is below 0.1% RH/min for a duration of 5 to 20 seconds.

In some embodiments, the microcontroller is further configured to modify the activation sequence according to a load-normalized energy $E_m(t)$ defined by Equation (3):

$$E_m(t) = \frac{P_{thermal}(t) + P_{PEF}(t) + P_{UAD}(t)}{M_{load}} \tag{3}$$

Where $P_{thermal}(t)$, $P_{PEF}(t)$, and $P_{UAD}(t)$ represent the energy consumption of the thermal unit, the PEF unit, and the UAD unit, respectively, $M_{load}$ represents the mass of the food load within the chambers.

The microcontroller is configured to attenuate the high-voltage pulses from the PEF unit when the load-normalized energy exceeds about 5 to 20 W/kg and limit the duty cycle from the UAD unit to about 40 to 60% when the load-normalized energy exceeds about 8 to 25 W/kg.

In some embodiments, the microcontroller is configured to compute the moisture content M(t) of the food load according to Equation (4):

$$M(t) = k_v \cdot v_{air}(t) \cdot [RH_{in}(t) - RH_{out}(t)] \cdot f(T_{ch}(t)) \tag{4}$$

Where $v_{air}(t)$ is the airflow velocity, $RH_{in}(t)$ and $RH_{out}(t)$ are inlet and outlet relative humidities, $T_{ch}(t)$ is the chamber temperature, $k_v$ is a calibration coefficient between 0.001 and 0.050 $kg \cdot m^{-3} \cdot s^{-1}$, $f(T_{ch}(t))$ is a temperature-dependent correction factor. The microcontroller is configured to update the moisture content M(t) at intervals between 0.5 and 5 seconds.

In another exemplary embodiment, a method for dehydrating food using a multi-modal dehydration device includes placing a food load into a chamber of a dehydrating cabinet. The chamber includes a thermal unit, a pulsed electric field (PEF) unit, an ultrasound-assisted dehydrating (UAD) unit, an airflow management unit, and an ultraviolet-C (UV-C) lamp. The method includes measuring a relative humidity gradient, a chamber temperature, and an airflow velocity via a sensing array. The sensing array includes a first humidity sensor positioned about 10 to 30 mm from an inlet port, a second humidity sensor positioned about 10 to 30 mm from an outlet port, a temperature sensor positioned about 5 to 30 mm from a sidewall of the chambers, and an airflow sensor disposed at an upper region of the sidewall of the chambers, about 20 to 50 mm from a surface level of an adjustable tray, controlling activation of the thermal unit, the PEF unit, and the UAD unit via a microcontroller according to Equation (2):

$$S(t) = \begin{cases} \text{Thermal}, & \text{if } \frac{dH}{dt} < \alpha \\ PEF, & \text{if } \frac{dH}{dt} \geq \text{and } \Delta T < \beta \\ UAD, & \text{if } H \leq \gamma \end{cases} \quad (2)$$

Where S(t) represents a mode-selection vector defining activation of the thermal unit, the PEF unit, and the UAD unit, $$\frac{dH}{dt}$$

is a humidity rate of change, ΔT is a temperature deviation, H is the relative humidity within the chamber, $\alpha$ is a humidity rate-of-change threshold, $\beta$ is a temperature-deviation threshold, $\gamma$ is a chamber-humidity threshold.

The microcontroller is configured to activate the thermal unit to raise the chamber temperature between 40° C. and 80° C. and initiate an activation sequence. The transition includes the activation sequence from the thermal unit to the PEF unit when the humidity rate-of-change threshold is between about 0.5 and 2.0% RH/min. The transition also includes the activation sequence from the PEF unit to the UAD unit when the temperature deviation is between 1° C. and 3° C. The transition further includes the activation sequence from the UAD unit to a termination state, when the chamber-humidity threshold is about 5% RH to 15% RH, adjusting the airflow velocity and a vent aperture based on the relative humidity gradient via the airflow management unit. The airflow management unit includes a variable-speed fan and an exhaust vent. The method further includes activating the UV-C lamp during low-temperature dehydrating cycles and disabling the UV-C lamp when the chamber is opened via a safety interlock mechanism. The method further includes terminating the activation sequence when the relative humidity is below the chamber-humidity threshold.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
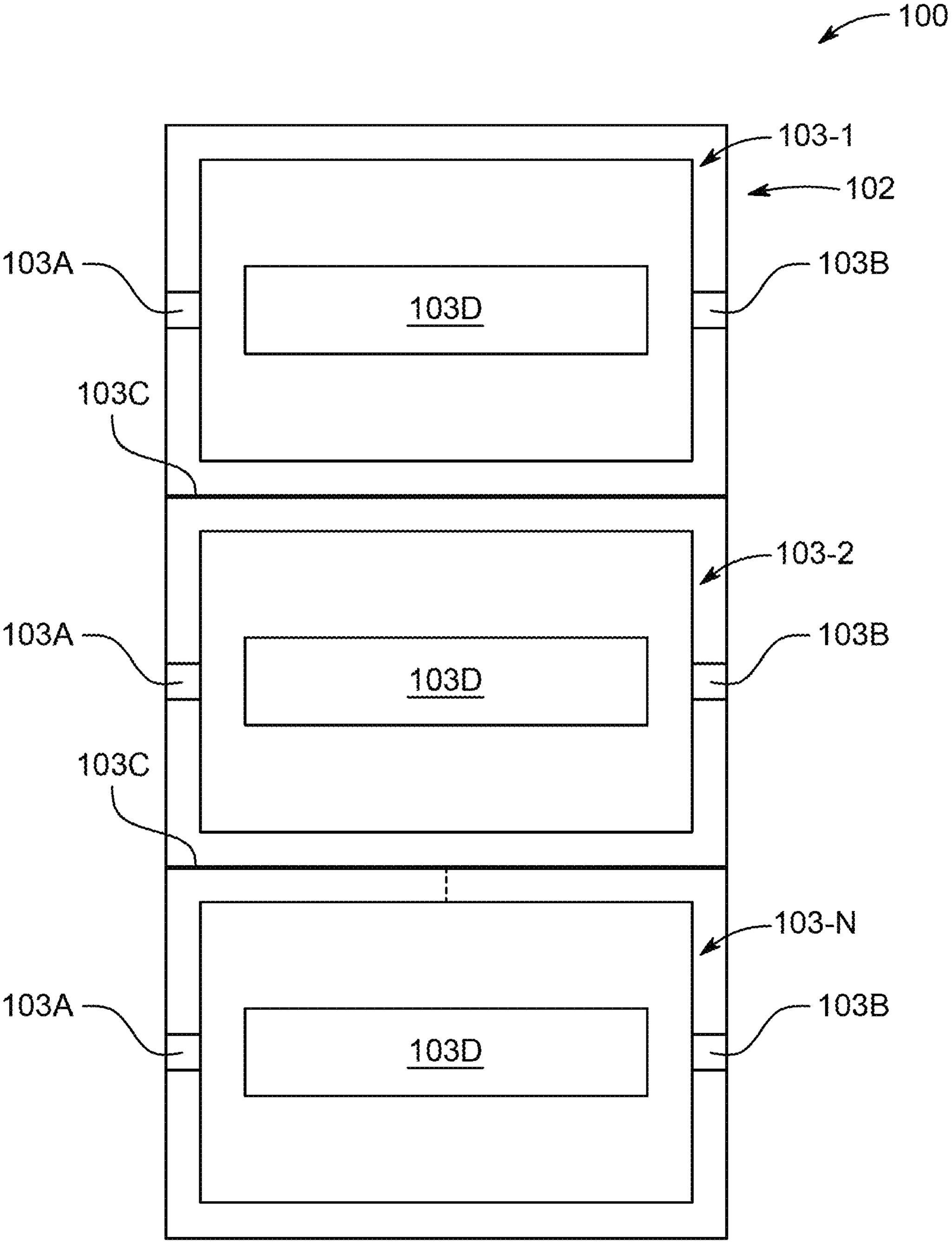
FIG. 1A is a schematic block diagram of a food dehydration device, according to certain embodiments.

In the drawings, reference numerals designate identical or corresponding parts throughout the several views. Further, as used herein, the words "a", "an" and the like carry a meaning of "one or more", unless stated otherwise.

Furthermore, the terms "approximately," "approximate", "about" and similar terms refer to ranges that include the identified value within a margin of 20%, 10%, or preferably 5%, and any values therebetween.

As used herein, the term "food dehydration" refers to the controlled removal of moisture from food products using thermal, non-thermal, or hybrid energy sources to reduce water activity and extend shelf life.

As used herein, the term "dehydrating cabinet" refers to an enclosed structural housing configured to contain one or more chambers in which food dehydration operations occur.

As used herein, the term "removable partition" refers to a thermally and/or moisture-insulating panel positioned between adjacent chambers and configured to be detached or repositioned without tools.

As used herein, the term "sensing array" refers to a collection of sensors disposed within a chamber and configured to measure environmental parameters, including humidity, temperature, and airflow.

As used herein, the term "humidity sensor" refers to any device configured to measure relative humidity or moisture content of air within a chamber.

As used herein, the term "temperature sensor" refers to any device configured to measure temperature within a chamber or proximate to a food load.

As used herein, the term "airflow sensor" refers to any device configured to measure airflow velocity or flow characteristics within a chamber.

As used herein, the term "dehydrating unit" refers to the combined set of components configured to remove moisture from food, including the thermal unit, the PEF unit, and the UAD unit.

As used herein, the term "thermal unit" refers to a heating subsystem configured to deliver heat energy to a chamber during dehydration.

As used herein, the term "pulsed electric field (PEF) unit" refers to a subsystem configured to apply high-voltage electrical pulses to food products to enhance moisture diffusion.

As used herein, the term "ultrasound-assisted dehydrating (UAD) unit" refers to a subsystem configured to generate ultrasonic energy within a chamber to promote moisture removal.

As used herein, the term "generate acoustic waves" refers to producing mechanical vibrations in the ultrasonic frequency range that propagate through air or chamber surfaces.

As used herein, the term "ultraviolet-C (UV-C) lamp" refers to a radiation-emitting device configured to generate UV-C wavelengths for microbial reduction or surface treatment.

As used herein, the term "low-temperature dehydrating cycles" refers to dehydration operations conducted at chamber temperatures below a predetermined threshold at which UV-C treatment may be applied.

As used herein, the term "safety interlock mechanism" refers to a hardware and/or electronic subsystem configured to detect an open-chamber condition and automatically deactivate UV-C, PEF, and UAD components.

As used herein, the term "airflow management unit" refers to a subsystem configured to generate, direct, and regulate airflow within and across chambers.

As used herein, the term "variable-speed fan" refers to a fan driven by a controllable motor whose rotational speed can be modulated to adjust airflow velocity.

As used herein, the term "exhaust vent" refers to a controllable outlet structure configured to regulate the discharge of moisture-laden air from a chamber.

As used herein, the term "energy module" refers to a subsystem configured to supply thermal or electrical energy to the device, including solar-thermal and electric heating components.

As used herein, the term "food load" refers to the quantity, mass, or arrangement of food items placed within a chamber for dehydration.

As used herein, the term "relative humidity" refers to the ratio of the amount of water vapor present in air to the maximum amount the air can hold at a given temperature.

As used herein, the term "cloud-based communication module" refers to a subsystem configured to transmit operational data, alerts, or control inputs between the device and a remote interface via a network.

As used herein, the term "thin-film resistive temperature detector (RTD)" refers to a temperature-sensing element formed from a thin conductive film whose electrical resistance varies with temperature.

As used herein, the term "a convective heating element" refers to a heating device configured to transfer heat to air that is circulated through a chamber.

As used herein, the term "forced airflow" refers to air movement generated by mechanical means rather than natural convection.

As used herein, the term "parallel-plate electrodes" refers to two conductive plates arranged with a defined spacing to generate an electric field when high-voltage pulses are applied.

As used herein, the term "high-voltage pulse generator" refers to a circuit or device configured to produce short-duration, high-voltage electrical pulses.

As used herein, the term "field strength" refers to the magnitude of the electric field generated between electrodes, expressed in kilovolts per centimeter.

As used herein, the term "pulse width" refers to the duration of an individual high-voltage pulse delivered by the PEF unit.

As used herein, the term "ultrasonic transducer" refers to a device that converts electrical energy into ultrasonic mechanical vibrations.

As used herein, the term "irradiance output" refers to the power of UV-C radiation emitted per unit area.

As used herein, the term "brushless DC (BLDC) motor actuator" refers to a motor that uses electronic commutation to drive a fan or actuator with variable speed.

As used herein, the term "a stepper-motor-driven actuator" refers to a motorized mechanism that adjusts vent aperture or airflow pathways in discrete angular steps.

As used herein, the term "solar irradiance" refers to the power per unit area of solar radiation incident on the solar thermal collector.

As used herein, the term "convective heat-exchange interface" refers to a structure or pathway through which heat is transferred from a heating source to air circulating within the chambers.

As used herein, the term "direct air-loop coupling" refers to a configuration in which heated air from the solar thermal collector is directly circulated into the dehydrating cabinet.

As used herein, the term "closed-loop thermal fluid circuit" refers to a sealed system in which a heat-transfer fluid circulates between the solar thermal collector and a heat exchanger.

As used herein, the term "multivariable proportional-integral-derivative (PID) control model" refers to a control algorithm that adjusts multiple outputs in response to proportional, integral, and derivative actions to humidity and temperature errors.

As used herein, the term "proportional gain matrix" refers to a matrix of coefficients that scale the immediate response of the control system to deviations in humidity and temperature.

As used herein, the term "integral gain matrix" refers to a matrix of coefficients that scale the accumulated error over time to eliminate steady-state deviations.

As used herein, the term "derivative gain matrix" refers to a matrix of coefficients that scale the predicted future error by the rates of change of humidity and temperature.

As used herein, the term "multi-condition gating" refers to a control strategy in which activation of a dehydration modality requires simultaneous satisfaction of two or more sensor-based conditions.

As used herein, the term "load-normalized energy" refers to the energy applied to the food load per unit mass, computed from the energy consumption of the thermal, PEF, and UAD units divided by the mass of the food load.

Aspects of this disclosure are directed to a food dehydration device. The food dehydration device includes multiple interconnected components that work together to remove moisture from food products during dehydration. The food dehydration device provides improved regulation of dehydration parameters such as temperature, humidity, and airflow, which may contribute to more uniform dehydration outcomes across different food loads and processing conditions. The food dehydration device may further support flexible operation through thermal and non-thermal treatment components, allowing adaptation to different food characteristics and dehydration objectives. The food dehydration device may improve energy utilization and operational safety while maintaining the consistency and repeatability of dehydration performance.

Referring to FIG. 1A, a schematic block diagram of a food dehydration device 100 is illustrated, according to certain embodiments.

The food dehydration device 100 refers to an apparatus configured to perform controlled, energy-efficient dehydration of food products with improved uniformity, safety, and shelf life. The food dehydration device 100 may be suitable for simultaneously dehydrating heterogeneous food types.

The food dehydration device 100 includes a dehydrating cabinet 102 including a plurality of chambers 103. The dehydrating cabinet 102 defines an enclosed structure configured to house the plurality of chambers 103 in a spaced or arranged configuration. Each chamber of the plurality of chambers 103 is configured to receive a food load for dehydration and may be formed as an individual compartment within the dehydrating cabinet 102.

In an embodiment, the plurality of chambers 103 includes a first chamber 103-1, a second chamber 103-2, a third chamber 103-3, and Nth chambers 103-N.

In an embodiment, the plurality of chambers 103 may be arranged in a stacked, side-by-side, or otherwise distributed manner within the dehydrating cabinet 102, such that the plurality of chambers 103 are accessible independently of one another. The dehydrating cabinet 102 may further provide structural support and environmental separation for the plurality of chambers 103 during operation of the food dehydration device 100.

Each chamber of the plurality of chambers 103 includes an inlet port 103A, an outlet port 103B, a removable partition 103C, and an adjustable tray 103D.

The inlet port 103A may be configured to introduce drying air. The outlet port 103B may be configured to exhaust moisture-laden air, and the adjustable tray 103D is configured to support food items. The adjustable tray 103D may be repositionable to accommodate food items of varying thickness and volume.

In some embodiments, the adjustable tray 103D is thermally isolated from the surrounding chamber walls to reduce conductive heat transfer and maintain uniform temperature distribution across the food load. The adjustable tray 103D is supported by a set of low-thermal-conductivity standoffs positioned along the chamber's sidewalls. The standoffs are formed from materials selected from the group consisting of a glass-fiber-reinforced polymer, a ceramic-filled polyetheretherketone (PEEK), a silica aerogel composite block, and a microporous ceramic insulation pad. The standoffs exhibit a thermal conductivity between 0.015 and 0.25 $W \cdot m^{-1} \cdot K^{-1}$, thereby limiting conductive heat transfer from the chamber walls to the tray. In some embodiments, the tray 103D includes a multi-layer structure comprising a stainless-steel support mesh bonded to a polymer-insulation underlayer having a thickness between 1.0 and 3.0 mm. This configuration minimizes thermal gradients across the tray surface and enables accurate temperature sensing by temperature sensor 114, which is positioned proximate to the tray.

In some embodiments, the plurality of chambers 103 is thermally isolated from one another by the removable partition 103C. The removable partition 103C is selected from the group including an aerogel-based insulation panel, a vacuum-insulated panel VIP, a ceramic-fiber insulation panel, or a silica-based microporous insulation panel. The removable partition 103C restricts thermal and moisture transfer between adjacent chambers of the plurality of chambers 103, enabling independent dehydration of different food types. The partitions are mounted in recessed channels formed in the dehydrating cabinet 102, enabling tool-free removal for cleaning or reconfiguration. The thermal isolation allows each chamber to operate at an independent temperature, humidity, and airflow profile. This enables simultaneous dehydration of heterogeneous food loads without cross-thermal interference.

In an embodiment, the dehydrating cabinet 102 is constructed from a corrosion-resistant material selected from stainless steel, aluminum alloy, or a polymer-metal composite. The dehydrating cabinet 102 encloses the plurality of chambers 103.

Figure 1B:
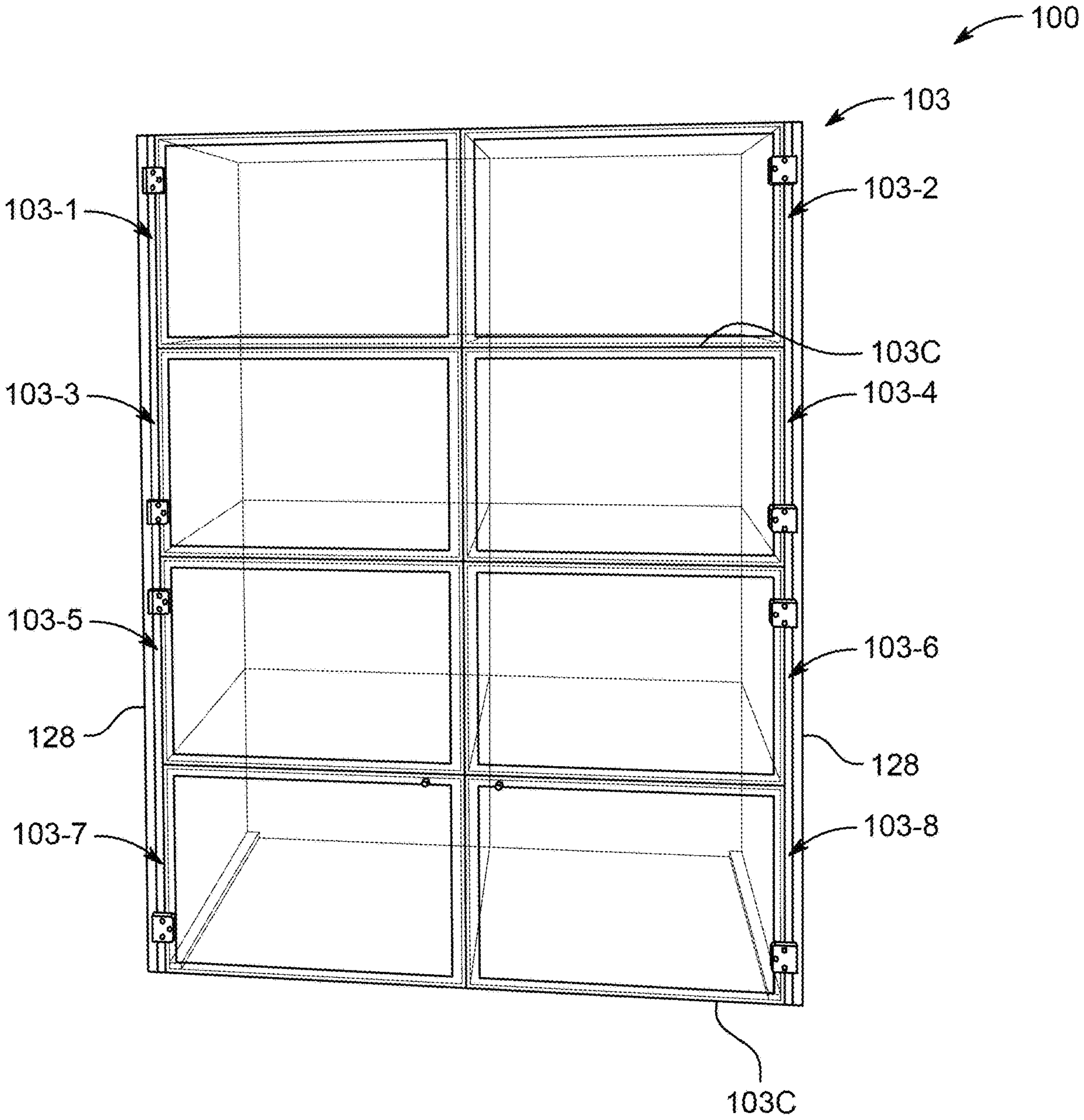
FIG. 1B is a front view of the food dehydration device, according to certain embodiments.

The dehydrating cabinet 102 includes one or more walls 128 (shown in FIG. 1B). One or more walls 128 have a thickness in a range between about 1.0 and 4.0 mm, preferably 1.2 and 3.8 mm, preferably 1.4 and 3.6 mm, preferably 1.6 and 3.4 mm, preferably 1.8 and 3.2 mm, and preferably 2.0 and 3.0 mm. The dehydrating cabinet 102 has an overall internal volume in a range between about 50 and 500 liters, preferably 70 and 480 liters, preferably 90 and 460 liters, preferably 110 and 440 liters, preferably 130 and 420 liters, and preferably 150 and 400 liters.

Each chamber of the plurality of chambers 103 within the dehydrating cabinet 102 has a width in a range between about 150 and 600 mm, preferably 170 and 580 mm, preferably 190 and 560 mm, preferably 210 and 540 mm, preferably 230 and 520 mm, and preferably 250 and 500 mm, a depth in a range between about 200 and 800 mm, preferably 240 and 760 mm, preferably 280 and 720 mm, preferably 320 and 680 mm, preferably 360 and 640 mm, preferably 400 and 600 mm, and a height in a range between about 150 and 700 mm, preferably 170 and 670 mm, preferably 190 and 640 mm, preferably 210 and 610 mm, preferably 230 and 580 mm, and preferably 250 and 550 mm.

Referring to FIG. 1B, a front view of the food dehydration device 100 is illustrated, according to certain embodiments.

In an embodiment, the dehydrating cabinet 102 includes eight chambers arranged in a stacked and/or arrayed configuration. The plurality of chambers 103 includes 103-1, 103-2, 103-3, 103-4, 103-5, 103-6, 103-7, and 103-8.

Each chamber 103-1 to 103-8 is structurally separated from an adjacent chamber by one or more walls 128, enabling independent or controlled dehydration conditions within each chamber. The number, arrangement, and configuration of the plurality of chambers 103 may vary based on application requirements, capacity needs, and manufacturing considerations.

Figure 1C:
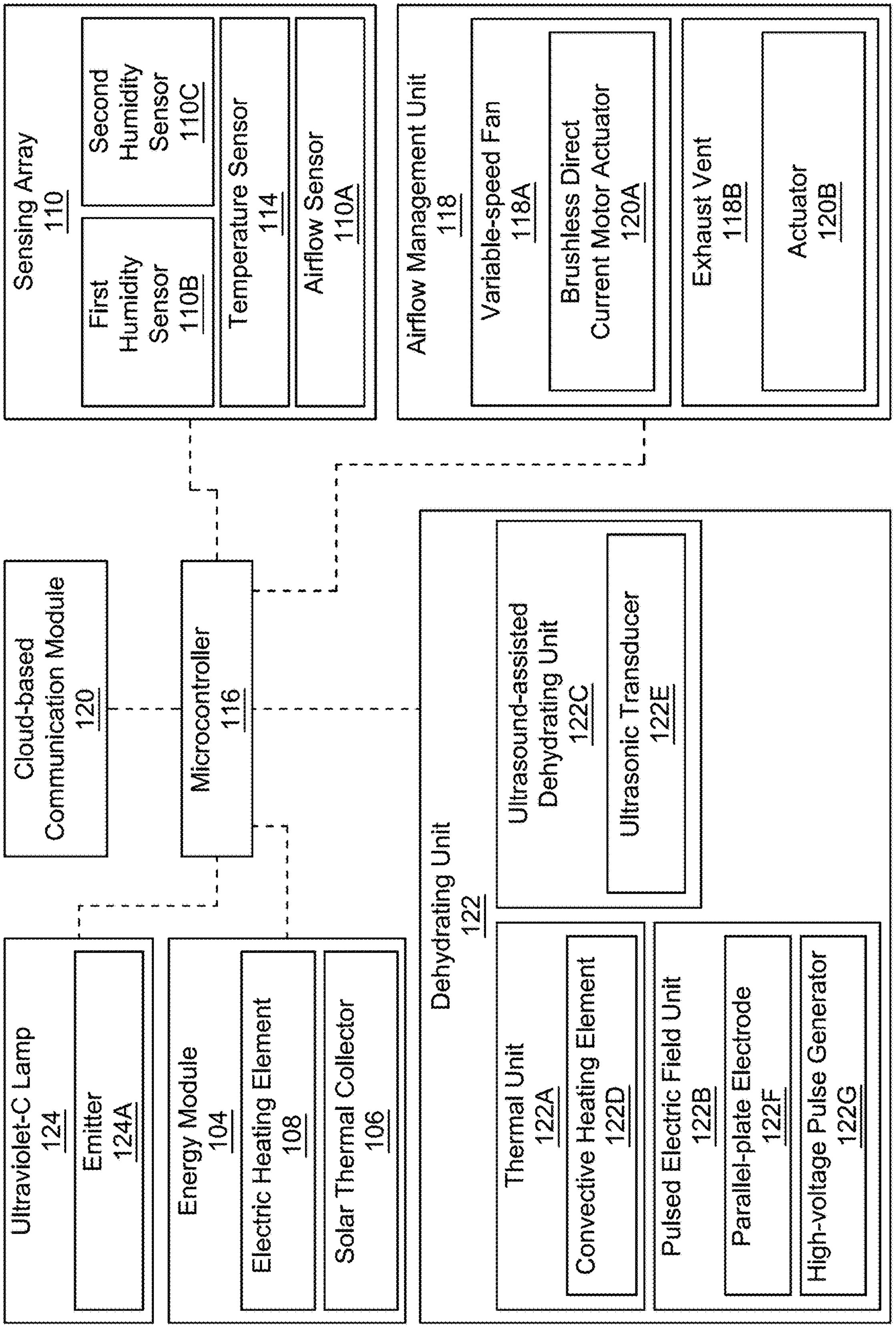
FIG. 1C is a schematic block diagram showing the operation connection with a microcontroller of the food dehydration device, according to certain embodiments.

Referring to FIG. 1C, a schematic block diagram showing the operation connection with a microcontroller 116 of the food dehydration device 100 according to certain embodiments.

The food dehydration device 100 further includes a sensing array 110 disposed within each of the plurality of chambers 102. The sensing array 110 is configured to monitor one or more environmental parameters within the corresponding chamber of the plurality of chambers 103 during a dehydration operation.

In an embodiment, each sensing array 110 includes humidity sensors 110B, 110C positioned at the inlet port

103A and the outlet port 103B and configured to measure a relative humidity gradient. The humidity sensors 110B and 110C are configured to measure relative humidity at the inlet port 103A and the outlet port 103B, respectively. Measurements obtained from the humidity sensors 112 may be used to determine a relative humidity gradient across the plurality of chambers 103 during operation of the food dehydration device 100.

The sensing array 110 further includes a temperature sensor 114 positioned at the adjustable tray 103D within the plurality of chambers 103. The temperature sensor 114 is configured to detect a chamber temperature of the corresponding chamber of the plurality of chambers 103, including a temperature proximate to a food load supported on the tray during operation of the food dehydration device 100.

The sensing array 110 further includes an airflow sensor 110A positioned at an upper region of a sidewall of the plurality of chambers 103. The airflow sensor 110A is configured to measure an airflow velocity within the plurality of chambers 103 during operation of the food dehydration device 100.

The airflow sensor 110A enables monitoring of airflow conditions in a region through which air circulates during a dehydration cycle. The airflow velocity measured by the airflow sensor 110A may indicate airflow distribution, circulation efficiency, or airflow uniformity within the plurality of chambers 103.

The food dehydration device 100 further includes an airflow management unit 118. The airflow management unit 118 is configured to control the movement of air within the food dehydration device 100 and through the plurality of chambers 103 during operation of the food dehydration device 100.

In some embodiments, the airflow management unit 118 is operatively coupled to the plurality of chambers 103 and configured to direct airflow through each chamber in a controlled manner. The airflow management unit 118 may be configured to introduce airflow into the plurality of chambers 103, circulate airflow within the chambers 103, and discharge airflow from the chambers 103 during a dehydration cycle.

The airflow management unit 118 may operate in coordination with the sensing array 110 to regulate airflow conditions within the plurality of chambers 103.

In a non-limiting exemplary embodiment, airflow parameters such as airflow velocity, flow rate, or distribution may be adjusted based on sensed operating conditions within the plurality of chambers 103.

The airflow management unit 118 includes a variable-speed fan 118A disposed at the inlet port 103A and the outlet port 103B. The variable-speed fan 118A is configured to drive air through the plurality of chambers 103. The variable-speed fan 118A is configured to generate the airflow velocity between 0.5 and 5.0 m/s, preferably 0.6 and 4.8 m/s, preferably 0.7 and 4.6 m/s, preferably 0.8 and 4.4 m/s, preferably 0.9 and 4.2 m/s, and preferably 01.0 and 4.0 m/s, and maintain a static pressure between 20 and 120 Pa, preferably 22 and 115 Pa, preferably 24 and 110 Pa, preferably 26 and 105 Pa, preferably 28 and 100 Pa, preferably 30 and 95 Pa.

The variable-speed fan 118A generates a controlled airflow that enters the plurality of chambers 103 through the inlet port 103A, circulates within the plurality of chambers 103, and exits through the outlet port 103B.

The variable-speed fan 118A includes a brushless direct current (BLDC) motor actuator 120A. The BLDC motor actuator 120A is selected from the group including a sensorless BLDC actuator, a Hall sensor-based BLDC actuator, a PWM-driven BLDC actuator, and a closed-loop BLDC actuator.

The airflow management unit 118 further includes an exhaust vent 118B disposed at the outlet port 103B of the plurality of chambers 103. The exhaust vent 118B includes actuators 120B configured to regulate an exhaust flow path.

The actuators 120B may be operable to vary an aperture size, flow restriction, or discharge direction associated with the exhaust vent 118B, thereby enabling controlled release of air from the plurality of chambers 103.

In one embodiment, the exhaust vent 118B includes a stepper motor-driven actuator. The stepper motor-driven actuator is selected from the group including a bipolar stepper motor, a unipolar stepper motor, a micro-stepping stepper motor, a permanent magnet stepper actuator, and a variable reluctance stepper actuator.

The exhaust vent 118A is configured to modulate the vent aperture between 5% and 95%, preferably 10% and 90%, preferably 15% and 85%, preferably 20% and 80%, and preferably 25% and 75% open, regulate exhaust flow rate about 0.1 to 1.5 $m^3$/min, preferably 0.2 to 1.4 $m^3$/min, preferably 0.3 to 1.3 $m^3$/min, preferably 0.4 to 1.2 $m^3$/min, and preferably 0.5 to 1.1 $m^3$/min, and maintain a pressure-balanced airflow across the plurality of chambers 103.

The vent aperture enables the exhaust vent 118B to maintain a pressure-balanced airflow across the plurality of chambers 103, thereby promoting uniform airflow distribution and consistent dehydration conditions.

The airflow management unit 118 is configured to modulate an airflow based on the relative humidity gradient between the inlet port 103A and the outlet port 103B. The relative humidity gradient may be determined from measurements obtained from the humidity sensors 110B and 110C in the sensing array 110. The airflow management unit 118 may adjust airflow conditions in response to changes in the relative humidity gradient during the dehydration cycle.

The airflow management unit 118 is further configured to adjust the fan speed of the variable-speed fan 118A and the vent aperture to maintain a uniform dehydrating condition across the plurality of chambers 103. Adjustment of fan speed and vent aperture may be performed dynamically to promote consistent airflow distribution, moisture removal, and dehydration performance across the plurality of chambers 103.

In some embodiments, the airflow management unit 118 includes a single variable-speed fan 118A positioned at the inlet port 103A and configured to draw or push air through the chamber. In other embodiments, the airflow management unit 118 includes a pair of variable-speed fans, one disposed at the inlet port 103A, and one disposed at the outlet port 103B, configured to operate in a coordinated push-pull configuration. The dual-fan configuration enables better control of static pressure and airflow velocity and helps remove moisture-laden air. The microcontroller 116 independently modulates the rotational speed of each fan to maintain a pressure-balanced airflow across the plurality of chambers 103.

In an embodiment, operation of the airflow management unit 118 is controlled by the microcontroller 116 based on data received from the sensing array 110 and selected dehydration parameters.

The food dehydration device 100 further includes a dehydrating unit 122 disposed in the plurality of chambers 103. The dehydrating unit 122 is configured to remove moisture from food products positioned within the respective plurality of chambers 103 during operation of the food dehydration device 100.

In an embodiment, the dehydrating unit 122 may be located fully or partially within each of the plurality of chambers 103 to deliver dehydration effects to the interior of the plurality of chambers 103.

The dehydrating unit 122 may be configured to operate continuously or intermittently during a dehydration cycle. The dehydrating unit 122 may be activated in coordination with other components of the food dehydration device 100 or may operate independently within each chamber of the plurality of chambers 103.

The food dehydration device 100 further includes an ultraviolet-C (UV-C) lamp 124 disposed in the plurality of chambers 103 and configured to activate during low-temperature dehydrating cycles.

The UV-C lamp 124 is configured to emit ultraviolet radiation within a wavelength range suitable for sanitizing or treating the plurality of chambers 103 during operation of the food dehydration device 100.

The UV-C lamp 124 is configured to activate during low-temperature dehydrating cycles in which the chamber temperature is maintained below a predetermined threshold. In such low-temperature dehydrating cycles, the UV-C lamp 124 may supplement the dehydration process by providing an additional treatment mechanism without increasing the thermal load within the plurality of chambers 103.

The UV-C lamp 124 may be positioned within each chamber of the plurality of chambers 103 such that emitted ultraviolet radiation is directed toward interior surfaces of the plurality of chambers 103 and toward food products supported on the adjustable trays 103D disposed therein.

In some embodiments, the UV-C lamp 124 may be mounted to a sidewall, ceiling region, or other interior surface of the plurality of chambers 103. The positioning and orientation of the UV-C lamp 124 may be adjusted to place food in the food dehydration device 100.

The UV-C lamp 124 includes at least one emitter 124A. The emitter 124A is selected from the group including a low-pressure mercury vapor emitter, a pulsed-xenon excimer emitter, a krypton-chloride excimer emitter, a UV-C light-emitting diode (LED) emitter, and a plasma discharge emitter.

The UV-C lamp 124 emits radiation in a range between 200 nm and 280 nm and has an irradiance output in a range between 0.5 and 3.0 $mW/cm^2$, preferably 0.6 and 3.0 $mW/cm^2$, preferably 0.7 and 2.8 $mW/cm^2$, preferably 0.8 and 2.6 $mW/cm^2$, preferably 0.9 and 2.4 $mW/cm^2$, and preferably 1.0 and 2.2 $mW/cm^2$.

The food dehydration device 100 further includes an energy module 104. The energy module 104 is disposed at a surface of the dehydrating cabinet 102 and configured to provide electrical energy to the food dehydration device 100 during operation.

In an embodiment, the energy module 104 may be integrated with the dehydrating cabinet 102 or may be mounted externally relative to the dehydrating cabinet 102. The energy module 104 may operate continuously or intermittently and may provide energy based on operating conditions or selected dehydration cycles.

In an embodiment, the energy module 104 includes a solar thermal collector 106. The solar thermal collector 106 is disposed at or on a surface of the dehydrating cabinet 102 and is thermally coupled to the dehydrating cabinet 102 to transfer thermal energy to the plurality of chambers 103.

In some embodiments, the energy module 104 includes a dual-mode solar-thermal coupling system configured to deliver thermal energy to the plurality of chambers 103 through either a direct air-loop coupling or a closed-loop thermal-fluid circuit.

In the direct air loop mode, the solar thermal collector 106 heats ambient air circulated through a dedicated air channel and introduced into the dehydrating cabinet 102. Heated air is conveyed into the plurality of chambers 103 via the inlet port 103A, supplementing or replacing heat generated by the thermal unit 122A.

In the closed-loop thermal-fluid mode, the solar thermal collector 106 heats a working fluid selected from the group consisting of water, glycol-water mixtures, and silicone-based heat-transfer fluids. The working fluid circulates through a heat-exchange coil thermally coupled to the dehydrating cabinet 102. The thermal-fluid circuit operates at a flow rate between 0.2 and 1.5 L/min, enabling controlled transfer of solar-derived heat to the chambers without introducing external air.

The microcontroller 116 dynamically selects between direct air-loop mode and closed-loop thermal-fluid mode based on chamber temperature, solar irradiance, and airflow requirements. When solar irradiance exceeds 300 $W/m^2$, the microcontroller 116 prioritizes solar-derived heating to reduce electrical energy consumption.

In one embodiment, the solar thermal collector 106 is thermally coupled to the dehydrating cabinet 102 to heat the plurality of chambers 103 through a convective heat exchange interface. The convective heat exchange interface enables heat generated by the solar thermal collector 106 to be conveyed to the air circulating within the plurality of chambers 103.

The convective heat exchange interface includes at least one of a direct air-loop coupling and a closed-loop thermal-fluid circuit. The thermal fluid circuit operates at a flow rate of about 0.2 to 1.5 L/min, preferably 0.3 to 1.4 L/min, preferably 0.4 to 1.3 L/min, preferably 0.5 to 1.2 L/min, preferably 0.6 to 1.1 L/min, and preferably 0.7 to 1.0 L/min.

In one embodiment, the direct air loop coupling conveys heated air into the plurality of chambers 103. In other embodiments, the closed-loop thermal fluid circuit circulates a heat transfer fluid to deliver thermal energy to the plurality of chambers 103, thereby enabling controlled and efficient heat exchange during dehydration operations.

The solar thermal collector 106 is configured to provide supplemental heating when solar irradiance exceeds 300 $W/m^2$. Under such conditions, thermal energy generated by the solar thermal collector 106 may be utilized to augment heat delivered by the thermal unit 122A or to reduce reliance on other energy sources during a dehydration cycle.

In an embodiment, the solar thermal collector 106 is selected from the group including a flat plate solar thermal collector 106, an evacuated tube solar collector, and a compound parabolic concentrator.

The energy module 104 further includes an electric heating element 108. The electric heating element 108 is configured to generate thermal energy for heating the plurality of chambers 103 during operation of the food dehydration device 100. The electric heating element 108 supplies heat energy independently of the solar thermal collector 106 or in combination therewith to support dehydration cycles under varying environmental conditions.

The electric heating element 108 may be disposed within the dehydrating cabinet 102 or adjacent to an airflow path associated with the plurality of chambers 103 such that generated heat is conveyed to the plurality of chambers 103 by convection.

The food dehydration device 100 further includes a microcontroller 116. The microcontroller 116 is configured to control the food dehydration device 100. The microcontroller 116 is configured to process sensor data, manage operating parameters, and coordinate activation of functional units during dehydration cycles. The dehydrating unit 122 includes a thermal unit 122A configured to deliver heat energy. The thermal unit 122A is operatively associated with the plurality of chambers 103 and is configured to generate and supply heat energy to the interior of the plurality of chambers 103 during operation of the food dehydration device 100.

The thermal unit 122A includes a convective heating element 122D configured to transfer heat energy to air flowing through the plurality of chambers 103. The convective heating element 122D may be positioned within or adjacent to an airflow path associated with the plurality of chambers 103 such that heated air is delivered to the plurality of chambers 103.

The convective heating element 122D is selected from the group including an electrical resistance heating coil, a ceramic heating element, a finned tubular heater, and a radiant-convective hybrid heater.

The thermal unit 122A is configured to deliver heat energy to the plurality of chambers 103 via forced airflow generated by the variable-speed fan 118A at an airflow velocity of about 0.5 to 5.0 m/s, preferably 0.6 to 4.8 m/s, preferably 0.7 to 4.6 m/s, preferably 0.8 to 4.4 m/s, preferably 0.9 to 4.2 m/s, and preferably 01.0 to 4.0 m/s. The thermal unit 122A operates at a power output between 300 and 1500 W, preferably 350 and 1450 W, c 400 and 1400 W, preferably 450 and 1350 W, and preferably 4500 and 1300 W. The thermal unit 122A attains a sufficient thermal response time to raise the chamber temperature from 25° C. to 60° C., preferably 25° C. to 55° C., preferably 25° C. to 50° C., and preferably 25° C. to 45° C., within about 2 to 6 minutes. The thermal unit 122A is configured to maintain the chamber temperature at about 40° C. to 80° C., preferably 45° C. to 75° C., preferably 50° C. to 70° C., and preferably 55° C. to 65° C. during dehydration.

In operation, the variable-speed fan 118A directs air across the thermal unit 122A and into the plurality of chambers 103, thereby transporting heat energy through the plurality of chambers 103 by convection. In one or more embodiments, the airflow generated by the variable-speed fan 118A has an airflow velocity of about 0.5 to 5.0 m/s, preferably 0.6 to 4.8 m/s, preferably 0.7 to 4.6 m/s, preferably 0.8 to 4.4 m/s, preferably 0.9 to 4.2 m/s, and preferably 1.0 to 4.0 m/s, within the plurality of chambers 103.

The dehydrating unit 122 further includes a pulsed electric field (PEF) unit 122B configured to deliver high-voltage pulses. The PEF unit 122B is configured to generate high-voltage pulses with a field strength between 0.5 and 5.0 kV/cm, preferably 0.6 and 4.8 kV/cm, preferably 0.7 and 4.6 kV/cm, preferably 0.8 and 4.4 kV/cm, preferably 0.9 and 4.2 kV/cm, and preferably 1.0 and 4.0 kV/cm, and a pulse width between 1 and 50 μs, preferably 2 and 48 μs, preferably 3 and 46 μs, preferably 4 and 44 μs, preferably 5 and 42 μs, and preferably 6 and 40 μs.

The PEF unit 122B includes parallel-plate electrodes 122F spaced between 5 and 25 mm, preferably 6 and 24 mm, preferably 7 and 23 mm, preferably 8 and 22 mm, preferably 9 and 21 mm, and preferably 10 and 20 mm, and it operates at a repetition rate between 10 and 500 Hz, preferably 30 and 450 Hz, preferably 50 and 400 Hz, preferably 70 and 3500 Hz, preferably 90 and 300 Hz, and preferably 100 and 2500 Hz. The parallel-plate electrode 122F is disposed within the plurality of chambers 103. The parallel-plate electrode 122F may be arranged to establish an electric field across the region where the food products are positioned. The spacing, orientation, and placement of the parallel-plate electrode 122F may be selected to generate a desired electric field distribution within the corresponding chamber of the plurality of chambers 103.

The PEF unit 122B further includes a high-voltage pulse generator 122G. The high-voltage pulse generator 122G may be electrically coupled to the parallel-plate electrode 122F.

In some embodiments, the high-voltage pulses generated by the PEF unit 122B may be applied intermittently or in a pulsed sequence during a dehydration cycle.

The PEF unit 122B may be controlled by the microcontroller 116 based on one or more operating parameters, including dehydration cycle selection, chamber temperature, or other sensed conditions within the plurality of chambers 103.

In an embodiment, the high-voltage pulse generator 122G is selected from the group consisting of a capacitor-discharge pulse generator, a Marx bank pulse generator, and a solid-state insulated-gate bipolar transistor (IGBT) pulse generator.

The dehydrating unit 122 further includes an ultrasound-assisted dehydrating UAD unit 122C configured to generate acoustic waves within the plurality of chambers 103 during operation of the food dehydration device 100. The UAD unit 122C is operatively associated with the plurality of chambers 103 and is configured to apply ultrasonic energy to food products disposed therein.

The UAD unit 122C includes at least one ultrasonic transducer 122E disposed on the sidewall of the plurality of chambers 103. The ultrasonic transducer 122E is configured to emit acoustic waves into the interior of the plurality of chambers 103. Placement of the ultrasonic transducer 122E on the sidewall enables transmission of acoustic energy through air toward the food products supported on the adjustable tray 103D. The ultrasonic transducer operates at a range of about 20 to 60 kHz, preferably 22 to 58 kHz, preferably 24 to 56 kHz, preferably 26 to 54 kHz, preferably 28 to 52 kHz, and preferably 30 to 50 kHz, and at a duty cycle of about 20% to 80%, preferably 25% to 75%, preferably 30% to 70%, preferably 35% to 65%, and preferably 40% to 60%.

The ultrasonic transducer 122E is selected from the group including a piezoelectric ceramic transducer, a piezoelectric composite transducer, a magnetostrictive transducer, and a thin-film MEMS ultrasonic transducer.

The food dehydration device 100 further includes a cloud-based communication module 120 configured to transmit performance data and system alerts to a remote display interface. The performance data may include operational parameters, sensor readings obtained from the sensing array 110, and status information associated with dehydration cycles.

The cloud-based communication module 120 is further configured to transmit an external input to the microcontroller 116. The external input may include control commands, configuration settings, or adjustments to operating parameters. In one or more embodiments, the cloud-based communication module 120 enables remote monitoring and control of the food dehydration device 100.

The microcontroller 116 is operatively coupled to the energy module 104, the sensing array 110, the UV-C lamp 124, the dehydrating unit 122, and the airflow management unit 118. The microcontroller 116 is configured to receive sensor data from the sensing array 110 and to generate control signals for regulating the operation of the energy module 104, the ultraviolet-C (UV-C) lamp 124, the dehydrating unit 122, and the airflow management unit 118 during dehydration cycles.

The microcontroller 116 is configured to compute power outputs for the dehydrating unit 122 and the airflow management unit 118. The microcontroller 116 is configured to calculate the moisture content of a food load, and dynamically adjust the relative humidity gradient, the chamber temperature, and the relative humidity within the plurality of chambers 103.

The microcontroller 116 includes a multivariable proportional-integral-derivative (PID) control model configured to compute the power output u(t) according to a mathematical expression (1):

$$u(t) = K_p e(t) + K_i \int_0^t e(\tau)\, d\tau + K_d \frac{de(t)}{dt} \tag{1}$$

where:

$$e(t) = \begin{bmatrix} e_H(t) \\ e_T(t) \end{bmatrix}$$

represents humidity and temperature error vectors, $$u(t) = \begin{bmatrix} u_F(t) \\ u_V(t) \end{bmatrix}$$

represents the power output applied to the thermal unit 122A and the airflow management unit 118, $K_p$ is a proportional gain matrix in a range of about 0.5 and 3.0, $K_i$ is an integral gain matrix in a range of about 0.01 $s^{-1}$ to 0.50 $s^{-1}$, and $K_d$ is a derivative gain matrix in a range of about 0.001 s to 0.10 s.

In some embodiments, the mathematical expression (1) utilizes humidity and temperature error vectors representing deviations between sensed values obtained from the sensing array 110 and corresponding target values. Based on these error vectors, the multivariable PID control model computes the power output to the thermal unit 122A and the airflow to the airflow management unit 118. Selection of the gain matrices enables dynamic adjustment of heating and airflow parameters to maintain desired dehydration conditions. The multivariable PID control model enables the microcontroller 116 to simultaneously regulate temperature, humidity, and airflow within the plurality of chambers 103.

The microcontroller 116 is configured to control activation of the thermal unit 122A, the PEF unit 122B, and the UAD unit 122C according to an activation sequence defined by Equation (2)

$$S(t) = \begin{cases} \text{Thermal}, & \text{if } \frac{dH}{dt} < \alpha \\ PEF, & \text{if } \frac{dH}{dt} \geq \alpha \text{ and } \Delta T < \beta \\ UAD, & \text{if } H \leq \gamma \end{cases} \tag{2}$$

where:

S(t) represents a mode-selection vector defining activation of the thermal unit 122A, the PEF unit 122B, and the UAD unit 122C, $$\frac{dH}{dt}$$

is a humidity rate of change,

ΔT is a temperature deviation,

H is the relative humidity within the plurality of chambers 103,

α is a humidity rate-of-change threshold in a range between about 0.5% RH/min and 2.0% RH/min, β is a temperature-deviation threshold in a range between about 1° C. and 3° C., and γ is a chamber-humidity threshold in a range between about 5% RH and 20% RH.

The mode selection vector S(t) is determined based on a humidity rate of change dH/dt, a temperature deviation ΔT, and a relative humidity H within the plurality of chambers 103, as measured by the sensing array 110. When the humidity rate of change, dH/dt, is less than a humidity rate-of-change threshold a, the microcontroller 116 activates the thermal unit 122A. When the rate of change of humidity, dH/dt, is greater than or equal to the threshold α and the temperature deviation, ΔT, is less than the temperature-deviation threshold β, the microcontroller 116 activates the pulsed electric field (PEF) unit 122B. When the relative humidity H within the plurality of chambers 103 is less than or equal to the chamber-humidity threshold γ, the microcontroller 116 activates the ultrasound-assisted dehydrating (UAD) unit 122C.

The microcontroller 116 is configured to transition the activation sequence, including from the thermal unit 122A to the PEF unit 122B, when the humidity rate of change exceeds the humidity rate-of-change threshold. The activation sequence further includes the PEF unit 122B being connected to the UAD unit 122C when the UAD unit 122C transitions to a termination state and the relative humidity deviates below the temperature-deviation threshold. The activation sequence further includes, from the UAD unit 122C, a transition to a termination state when the relative humidity is below the chamber-humidity threshold. The transition may indicate that thermal dehydration has reached a condition in which non-thermal treatment is advantageous. This transition enables continued moisture removal while limiting additional thermal input to the plurality of chambers 103. Upon reaching the termination state, the microcontroller 116 may deactivate the dehydrating unit 122 and initiate completion or shutdown of the dehydration cycle.

The microcontroller 116 is further configured to apply a multi-condition gating to the activation sequence, initiating the thermal unit 122A to raise the chamber temperature between 40° C. and 80° C., preferably 45° C. to 75° C., preferably 50° C. to 70° C., and preferably 55° C. to 65° C. Initiating the PEF unit when the humidity rate of change exceeds a humidity-rate-of-change threshold in a range between 0.5 and 2.0% RH/min, preferably 0.6 and 1.9% RH/min, preferably 0.7 and 1.8% RH/min, preferably 0.8 and 1.7% RH/min, preferably 0.9 and 1.6% RH/min, and preferably 1.0 and 1.5% RH/min.

The chamber temperature is between 35° C. and 50° C. Initiating the UAD unit when the temperature deviation remains within the temperature-deviation threshold between 1° C. and 3° C. The relative humidity gradient between the inlet and outlet ports is about 3.0 to 15% RH, preferably 3.5 to 14% RH, preferably 4.0 to 13% RH, preferably 4.5 to 12% RH, preferably 5.0 to 11% RH, and preferably 5.5 to 10% RH. Maintaining the UAD unit while the relative humidity decreases at a rate between 0.2 and 1.0% RH/min, preferably 0.25 and 1.0% RH/min, preferably 0.3 and 1.0% RH/min, preferably 0.35 and 1.0% RH/min, and preferably 0.4 and 1.0% RH/min, and the airflow velocity remains between 0.5 and 3.0 m/s, preferably 0.6 and 2.9 m/s, preferably 0.7 and 2.8 m/s, preferably 0.8 and 2.7 m/s, preferably 0.9 and 2.6 m/s, and preferably 1.0 and 2.5 m/s. Terminating the activation sequence when either the relative humidity is below a termination threshold between 5 and 15% RH, preferably 5.5 to 14% RH, preferably 6.0 to 13% RH, preferably 6.5 to 12% RH, and preferably 7.0 to 11% RH. or the humidity rate of change is below 0.1% RH/min for a duration of 5 to 20 seconds. The gating condition enables application of the pulsed electric field (PEF) unit 122B under controlled thermal conditions.

The microcontroller 116 computes a relative humidity gradient ΔH(t) using measurements from the first humidity sensor 110B and the second humidity sensor 110C. The gradient is defined as:

$$\Delta H(t) = RH_{in}(t) - RH_{out}(t)$$

When the relative humidity gradient exceeds a threshold between 3% RH and 15% RH, the microcontroller 116 increases the rotational speed of the variable-speed fan 118A and opens the exhaust vent 118B to enhance moisture removal. When the relative humidity gradient falls below the threshold, the microcontroller 116 reduces fan speed and partially closes the exhaust vent 118B to maintain stable chamber humidity and prevent over-drying.

The microcontroller 116 initiates activation of the ultrasound-assisted dehydrating (UAD) unit 122C when a temperature deviation remains within a temperature-deviation threshold selected between about 1° C. and about 3° C. and when a relative humidity gradient between the inlet port 103A and the outlet port 103B is within a range of about 3% RH to about 15% RH.

The microcontroller 116 terminates the activation sequence when either the relative humidity within the plurality of chambers 103 falls below a termination threshold selected between about 5% RH and about 15% RH, or when the humidity rate of change is below about 0.1% RH/min for a duration between about 5 seconds and about 20 seconds. Upon termination, the microcontroller 116 may deactivate the dehydrating unit 122 and transition the food dehydration device 100 to a completion or standby state.

The microcontroller 116 is further configured to modify the activation sequence according to a load-normalized energy $E_m(t)$ defined by Equation (3):

$$E_m(t) = \frac{P_{thermal}(t) + P_{PBF}(t) + P_{UAD}(t)}{M_{load}} \quad (3)$$

where:

$P_{thermal}(t)$, $P_{PEF}(t)$, and $P_{UAD}(t)$ represent an energy consumption of the thermal unit 122A, The mass M load is obtained from a user input, a predefined recipe profile, or an estimated value derived from sensor data processed by the microcontroller 116. The load-normalized energy $E_m(t)$ enables the microcontroller 116 to scale activation duration, duty cycle, and sequencing of the thermal unit 122A, the PEF unit 122B, and the UAD unit 122C as a function of energy consumed per unit mass of the food load.

The load-normalized energy $E_m(t)$ defined in Equation (3) represents the instantaneous or cumulative energy applied to the food load per unit mass. The microcontroller 116 computes $E_m(t)$ using real-time power-consumption data obtained from:

- a current-sensing module coupled to the thermal unit 122A,
- a high-voltage pulse-monitoring circuit associated with the PEF unit 122B, and
- a drive-signal monitoring circuit associated with the UAD unit 122C.

The mass $M_{load}$ is obtained from:

- a load cell integrated beneath the adjustable tray 103D,
- an user-entered mass value, or
- an estimated mass derived from moisture-content modeling.

The microcontroller 116 updates $E_m(t)$ at intervals between 0.5 and 5 seconds, enabling dynamic adjustment of PEF pulse amplitude, UAD duty cycle, and thermal-unit power output based on energy-efficiency constraints.

The microcontroller 116 is configured to attenuate the high-voltage pulses from the PEF unit when the load-normalized energy exceeds about 5 to 20 W/kg, 6 to 19 W/kg, preferably 7 to 18 W/kg, preferably 8 to 17 W/kg, preferably 9 to 16 W/kg, and preferably 10 to 15 W/kg. The microcontroller 116 is configured to limit the duty cycle from the UAD unit to about 40 to 60% when the load-normalized energy exceeds about 8 to 25 W/kg, preferably 9 to 24 W/kg, preferably 10 to 23 W/kg, preferably 11 to 22 W/kg, preferably 12 to 21 W/kg, and preferably 13 to 20 W/kg.

The microcontroller 116 is configured to compute the moisture content M (t) of the food load according to Equation (4):

$$M(t) = k_v \cdot v_{air}(t) \cdot [RH_{in}(t) - RH_{out}(t)] \cdot f(T_{ch}(t)) \quad (4)$$

where:

$v_{air}(t)$ is the airflow velocity, $RH_{in}(t)$ and $RH_{out}(t)$ are inlet and outlet relative humidities, $T_{ch}(t)$ is the chamber temperature, $k_v$ is a calibration coefficient in a range between 0.001 and 0.050 kg $m^{-3} \cdot s^{-1}$ $f(T_{ch}(t))$ is a temperature-dependent correction factor.

The temperature-dependent correction factor f(T) used in Equation (5) represents the influence of chamber temperature on moisture-evaporation kinetics. In some embodiments, f(T) is modeled as a dimensionless exponential scaling factor expressed as:

$$f(T) = \exp[k_T(T - T_0)] \quad (5)$$

where:

$k_T$ is a temperature-sensitivity coefficient between 0.01 and 0.05° C.$^{-1}$, and $T_0$ is a reference temperature between 25° C. and 35° C.

In other embodiments, f(T) is implemented as a lookup table stored in memory associated with the microcontroller 116, wherein the lookup table maps chamber temperature values to empirically determined correction factors derived from calibration experiments. The correction factor compensates for temperature-dependent variations in vapor pressure, boundary-layer thickness, and convective transfer coefficients.

The microcontroller 116 is configured to update the moisture content M(t) at intervals in a range between 0.5 and 5 seconds.

The computed moisture content M(t) is used by the microcontroller 116 to adjust the operating parameters of the dehydrating unit 122 and the airflow management unit 118, and to determine transition points within the activation sequence, terminate dehydration, or generate system alerts.

In some embodiments, the microcontroller 116 implements a multi-condition gating algorithm to coordinate activation of the thermal unit 122A, the PEF unit 122B, and the UAD unit 122C. The algorithm evaluates multiple sensor inputs simultaneously to ensure that each dehydration modality is activated only under conditions that maximize efficiency and safety.

The multi-condition gating algorithm evaluates the humidity rate of change dH/dt, temperature deviation ΔT, relative humidity gradient ΔH, airflow velocity $v_{air}$, and chamber humidity H. The microcontroller 116 initiates the PEF unit 122B only when both the humidity rate of change exceeds a threshold between about 0.5 and 2.0% RH/min, and the chamber temperature is between 35° C. and 50° C. The microcontroller 116 initiates the UAD unit 122C only when both the temperature deviation remains within 1° C. to 3° C., and the relative humidity gradient between the inlet and outlet ports is between 3% RH and 15% RH. The UAD unit 122C is maintained only while the relative humidity decreases at a rate between 0.2 and 1.0% RH/min, and the airflow velocity remains between 0.5 and 3.0 m/s. The activation sequence terminates when chamber humidity falls below 5-15% RH, or the humidity rate of change remains below 0.1% RH/min for 5-20 seconds. This multi-condition gating ensures that each modality operates only when its physical mechanism is most effective.

Figure 1D:
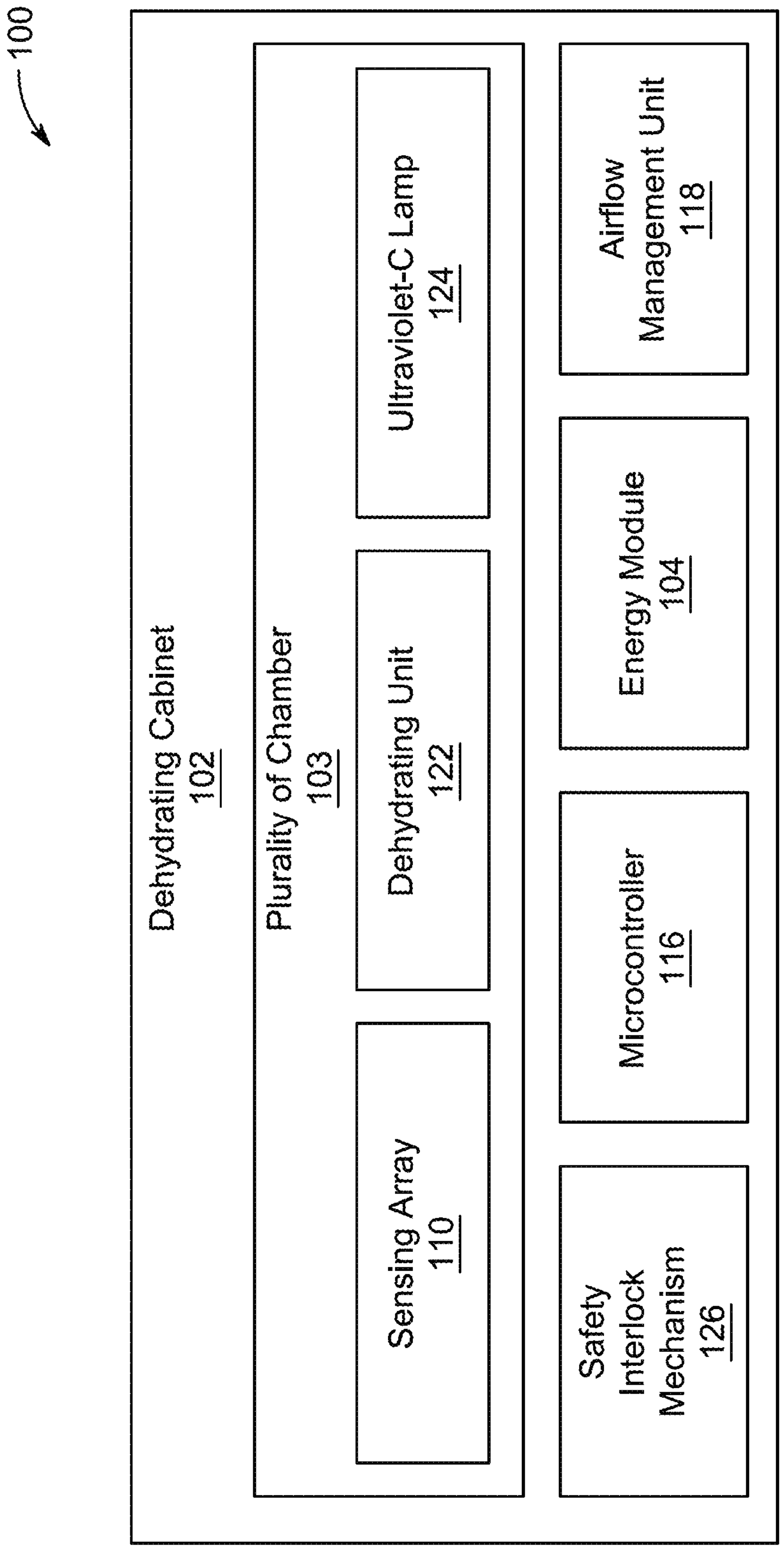
FIG. 1D is a schematic block diagram of the food dehydration device showing a safety interlock mechanism, according to certain embodiments.

Referring to FIG. 1D, a schematic block diagram of the food dehydration device 100 showing a safety interlock mechanism is illustrated, according to certain embodiments.

In some embodiments, the safety interlock mechanism 126 is configured to prevent user exposure to ultraviolet radiation, high-voltage pulses, and acoustic energy during operation. The safety interlock mechanism 126 is operatively coupled to each chamber door of the plurality of chambers 103 and is configured to detect an open-chamber condition.

Upon receiving the interlock signal, the microcontroller 116 is configured to immediately deactivate the ultraviolet-C lamp 124, the pulsed electric field (PEF) unit 122B, and the ultrasound-assisted dehydrating (UAD) unit 122C. In some embodiments, the microcontroller 116 also reduces the power output of the thermal unit 122A to a safe standby level to prevent accidental contact with heated surfaces. The interlock logic ensures that no non-thermal or high-energy treatment is applied while the chamber is accessible, thereby maintaining user safety and compliance with applicable radiation-exposure and electrical-safety standards.

In some embodiments, the safety interlock mechanism 126 is configured to deactivate the UV-C lamp 124 when a corresponding chamber of the plurality of chambers 103 is open. The safety interlock mechanism 126 is operatively associated with the plurality of chambers 103 and is configured to detect an open condition of each chamber of the plurality of chambers 103.

The safety interlock mechanism 126 includes at least one selected from the group, including a magnetic reed switch, a mechanical microswitch, an optical proximity sensor, and a Hall effect sensor.

Deactivation of the ultraviolet-C (UV-C) lamp 124 may occur immediately upon detection of the open condition, thereby inhibiting emission of ultraviolet radiation from the ultraviolet-C (UV-C) lamp 124 when the corresponding chamber of the plurality of chambers 103 is accessible.

Figure 2A:
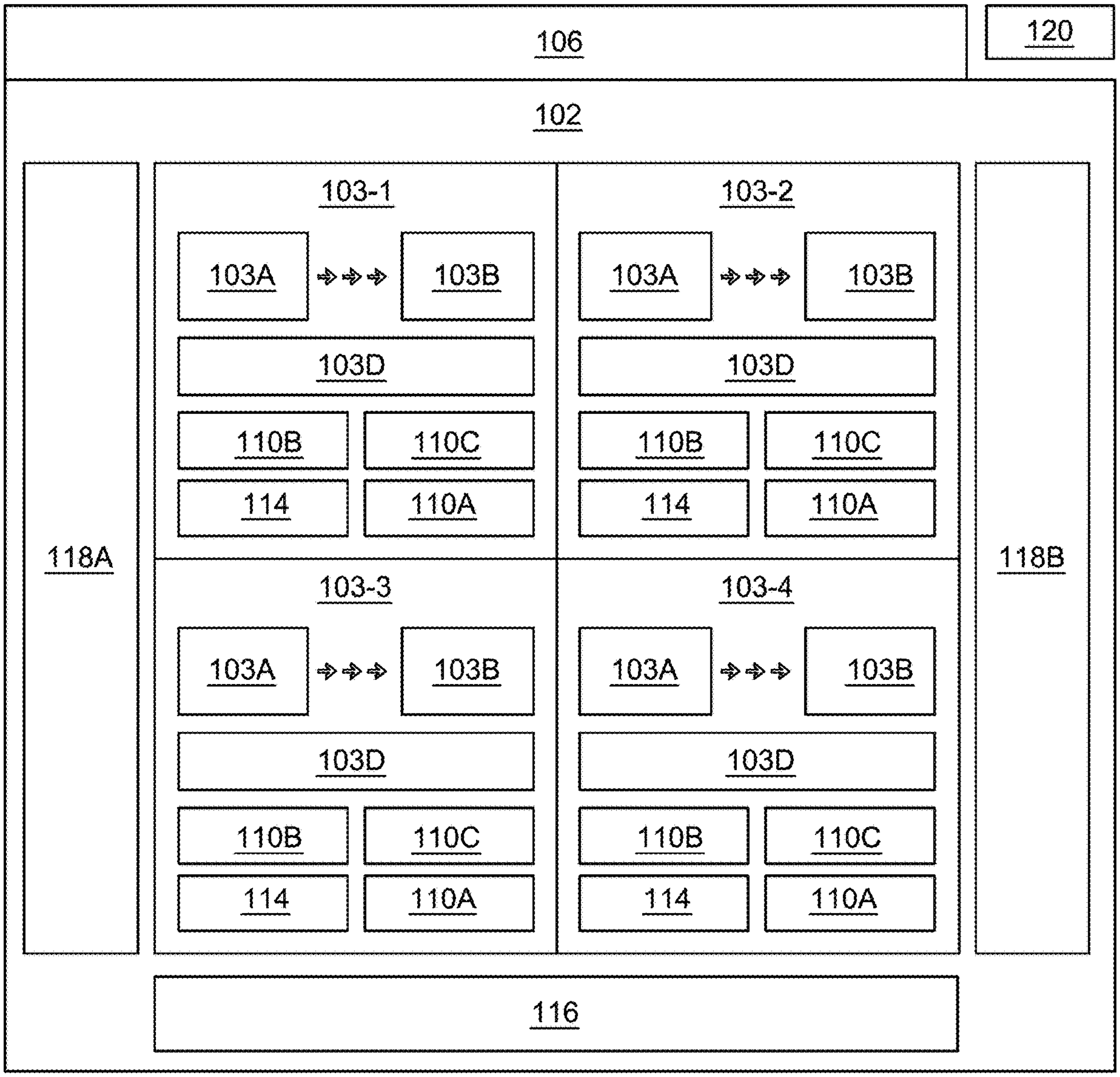
FIG. 2A is a schematic block diagram of the food dehydration device showing a cloud-based communication module, according to certain embodiments.

Referring to FIG. 2A, a schematic block diagram of the food dehydration device 100 showing the cloud-based communication module 120, is illustrated, according to certain embodiments.

In an embodiment, the cloud-based communication module 120 may include a communication interface selected from a Wi-Fi module, a cellular communication module, or a Bluetooth transceiver.

The cloud-based communication module 120 is configured to receive control commands, firmware updates, and operating profiles from a remote user device or cloud platform, enabling remote monitoring, predictive maintenance, data logging, and adaptive optimization of dehydration cycles.

In some embodiments, the cloud-based communication module 120 further supports secure data transmission via encryption protocols and authentication mechanisms to ensure reliable and secure communication between the food dehydration device 100 and the cloud infrastructure.

The humidity sensors 110B, 110C of the sensing array 110 include a first humidity sensor 110B positioned about 5 to 20 mm, preferably 6 to 19 mm, preferably 7 to 18 mm, preferably 8 to 17 mm, preferably 9 to 16 mm, and preferably 10 to 15 mm from the inlet port 103A. The humidity sensors 110B, 110C further include a second humidity sensor 110C positioned about 5 to 20 mm, preferably 6 to 19 mm, preferably 7 to 18 mm, preferably 8 to 17 mm, preferably 9 to 16 mm, and preferably 10 to 15 mm from the outlet port 103B. Such spatial positioning enables the sensing array 110 to capture localized relative humidity conditions in the incoming and outgoing airflow within each chamber of the plurality of chambers 103.

The first humidity sensor 110B is configured to measure an inlet relative humidity associated with air entering the chamber of the plurality of chambers 103, while the second humidity sensor 110C is configured to measure an outlet relative humidity associated with air exiting the chamber of the plurality of chambers 103. The microcontroller 116 is configured to process signals from the first humidity sensor 110B and the second humidity sensor 110C to determine a relative humidity gradient across the chamber of the plurality of chambers 103. This relative humidity gradient is used to estimate moisture-removal efficiency, regulate airflow via the airflow management unit 118, and dynamically adjust the operating parameters of the dehydrating unit 122 to maintain uniform, controlled dehydration conditions within the plurality of chambers 103.

Figure 2B:
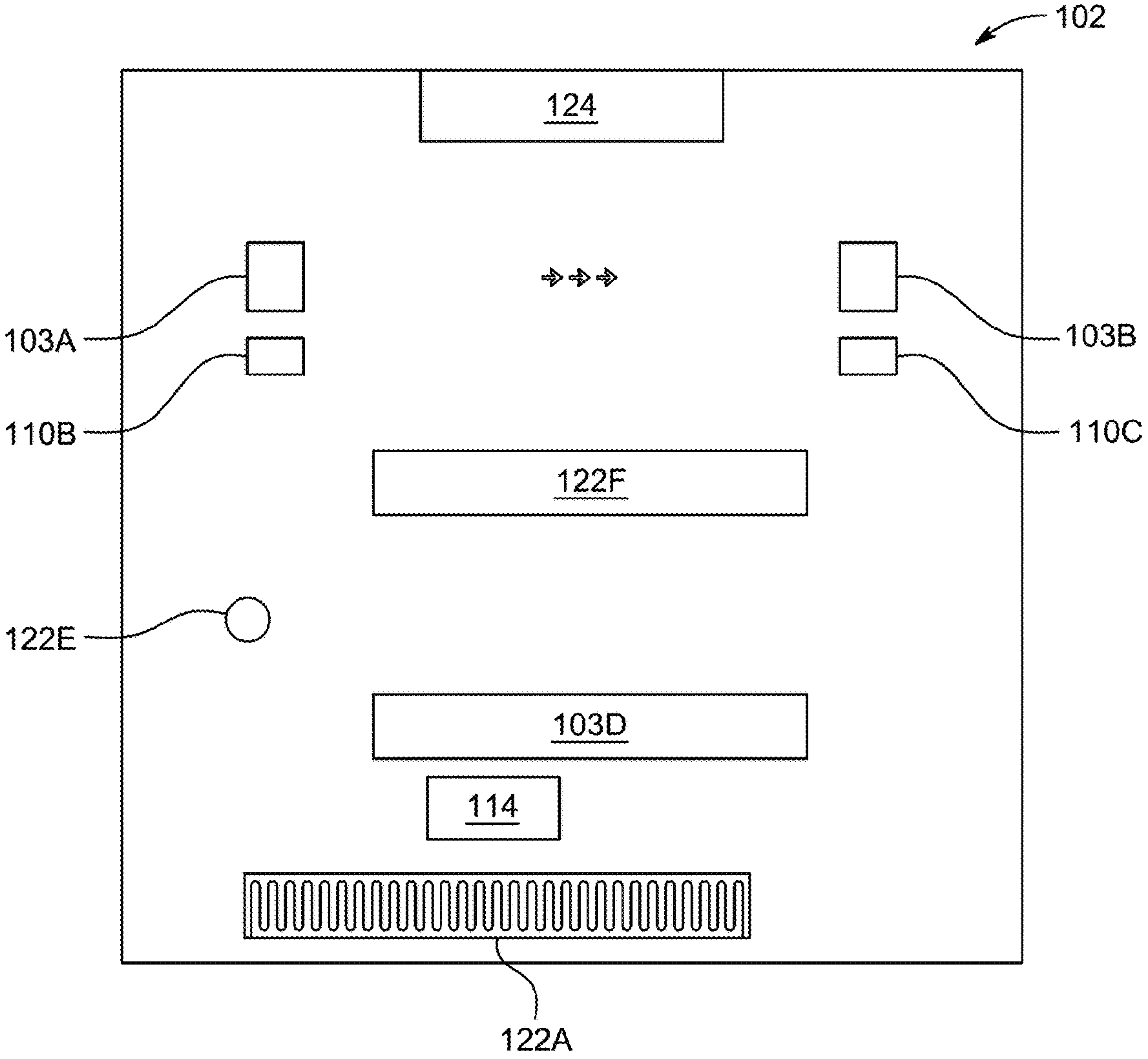
FIG. 2B is a schematic block diagram showing at least one ultrasonic transducer and a ultraviolet-C lamp of the food dehydration device, according to certain embodiments.

Referring to FIG. 2B, a schematic block diagram showing the ultrasonic transducer 122E and the ultraviolet-C lamp 124 of the food dehydration device 100 is illustrated, according to certain embodiments.

In some embodiments, the ultraviolet-C (UV-C) lamp 124 may be configured as a low-pressure mercury vapor lamp, a UV-C LED array, or a hybrid germicidal irradiation module operable within a wavelength range between about 200 to 280 nm.

In some embodiments, the UV-C lamp 124 may be positioned within an upper region of the chamber 103 to enhance irradiation uniformity across the food load and to minimize shadowing effects.

In some embodiments, the ultrasonic transducer 122E may include a secondary heat-assisted drying module including an infrared heating element, a resistive coil assembly, or a convective thermal plate configured to provide localized supplemental heating. In some embodiments, the thermal unit 122A may include a hybrid thermal exchange system configured to generate and distribute heated air within the plurality of chambers 103. The thermal unit 122A may further include thermal insulation layers and airflow-directing ducts configured to maintain substantially uniform thermal distribution during dehydration cycles.

Figure 2C:
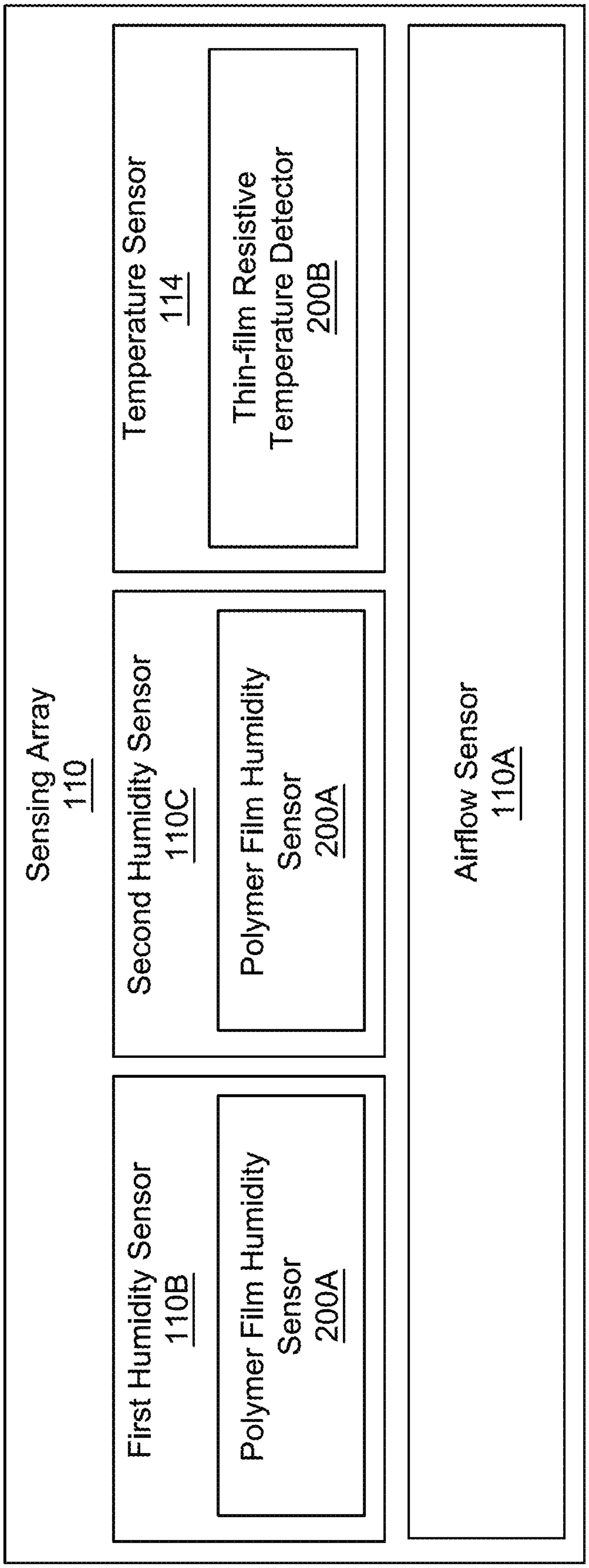
FIG. 2C is a schematic block diagram showing a sensing array of the food dehydration device, according to certain embodiments.

Referring to FIG. 2C, a schematic block diagram showing the sensing array 110 of the food dehydration device 100 is illustrated, according to certain embodiments.

The humidity sensors 110B and 110C also include a polymer film humidity sensor 200A. The polymer film humidity sensor 200A may be configured to detect relative humidity within each chamber of the plurality of chambers 103.

The polymer film humidity sensor 200A is selected from the group including a polyimide-based capacitive humidity sensor, a polyethylene terephthalate (PET) based capacitive humidity sensor, a polyvinyl alcohol (PVA) based capacitive humidity sensor, a cellulose acetate-based capacitive humidity sensor, and a fluoropolymer-based capacitive humidity sensor.

In an embodiment, the humidity sensors 110B, 110C have a sensing area of about 4 to 25 $mm^2$, preferably 6 to 23 $mm^2$, preferably 8 to 21 $mm^2$, preferably 10 to 19 $mm^2$, and preferably 12 to 17 $mm^2$. The sensing area is configured to provide sufficient exposure to airflow within the plurality of chambers 103 while maintaining rapid response time and measurement stability.

The temperature sensor 114 is disposed at the adjustable tray 103D about 5 to 30 mm, preferably 6 to 29 mm, preferably 7 to 28 mm, preferably 8 to 27 mm, preferably 9 to 26 mm, and preferably 10 to 25 mm from the sidewall of the plurality of chambers 103.

The positioning of the temperature sensor 114 enables to accurately detect the chamber temperature representative of the thermal environment experienced by the food load during dehydration. By locating the temperature sensor 114 proximate to the adjustable tray 103D and offset from the sidewall of the plurality of chambers 103, thermal gradients caused by wall heat conduction are minimized. The temperature measurements obtained by the temperature sensor 114 are transmitted to the microcontroller 116, which uses the temperature to regulate the operation of the thermal unit 122A, coordinate the activation of the PEF unit 122B and the UAD unit 122C, and maintain target temperature profiles throughout the dehydration cycle.

In an embodiment, the temperature sensor 114 includes a thin-film resistive temperature detector (RTD) 200B. The thin-film RTD 200B is selected from the group, which includes a platinum thin-film RTD, a nickel thin-film RTD, a copper thin-film RTD, a graphene-based thermoresistive temperature sensor 114, and an MXene-based thermoresistive temperature sensor 114. The temperature sensor 114 has a sensing area between 3 and 20 $mm^2$, preferably 5 and 19 $mm^2$, preferably 6 and 18 $mm^2$, preferably 7 and 17 $mm^2$, preferably 8 and 16 $mm^2$, and preferably 9 and 15 $mm^2$.

The airflow sensor 110A is disposed at the sidewall of the plurality of chambers 103, about 20 to 50 mm, preferably 22 to 48 mm, preferably 24 to 46 mm, preferably 26 to 44 mm, preferably 28 to 42 mm, and preferably 30 to 40 mm from the surface level of the tray. The airflow sensor 110A has a sensing area between about 3 and 20 $mm^2$, preferably 5 and 19 $mm^2$, preferably 6 and 18 $mm^2$, preferably 7 and 17 $mm^2$, preferably 8 and 16 $mm^2$, and preferably 9 and 15 $mm^2$, which provides a balance between measurement sensitivity and minimal disruption to airflow characteristics within the chamber of the plurality of chambers 103. The airflow sensor 110A responds rapidly to changes in airflow velocity generated by the variable-speed fan 118A while maintaining low flow resistance. Signals generated by the airflow sensor 110A are communicated to the microcontroller 116 and are used to regulate the operation of the airflow management unit 118, compute the moisture content of the food load, and maintain uniform dehydrating conditions across the plurality of chambers 103.

The airflow sensor 110A is selected from the group including a thermal anemometric airflow sensor 110A, a MEMS-based airflow sensor 110A, a hot wire airflow sensor 110A, a piezoresistive differential pressure airflow sensor 110A, and an ultrasonic time of flight airflow sensor 110A.

In an embodiment, each sensor of the sensing array 110 is encapsulated in a polymer coating selected from the group including a parylene C conformal coating, a silicone-based encapsulant, and a fluoropolymer coating. The encapsulation enhances sensor durability, maintains measurement accuracy under elevated humidity and temperature conditions, and extends the operational lifespan of the sensing array 110.

Figure 2D:
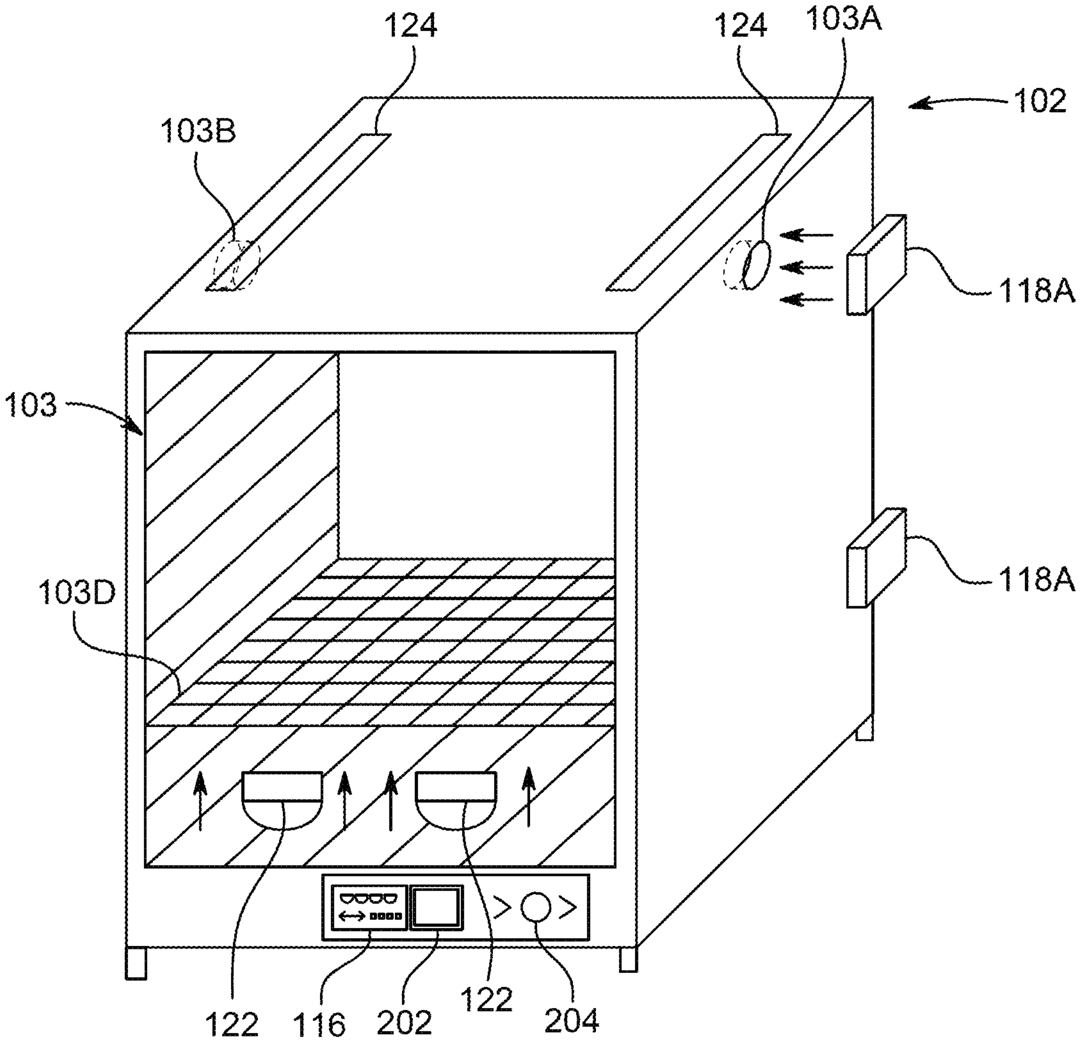
FIG. 2D is a perspective view showing a display and the microcontroller of the food dehydration device, according to certain embodiments.

Referring to FIG. 2D, a perspective view showing a display 202 and the microcontroller 116 of the food dehydration device 100, is illustrated, according to certain embodiments.

In an embodiment, the plurality of chambers 103 is fluidically coupled to an internal airflow pathway to enable controlled circulation of conditioned air between each chamber of the plurality of chambers 103.

The UV-C lamp 124 is disposed within an upper interior region of the dehydrating cabinet 102 and positioned to provide germicidal irradiation across the plurality of chambers 103. The UV-C lamp 124 may be mounted within a protective housing that includes a reflective inner surface configured to direct UV-C radiation toward the exposed surfaces of the food load and the interior chamber walls.

The variable-speed fan 118A is positioned adjacent to a sidewall portion of the dehydrating cabinet 102 and configured to generate a forced airflow stream through the plurality of chambers 103. The variable-speed fan 118A is operatively controlled by the microcontroller 116 to regulate airflow velocity, pressure distribution, and uniform air circulation across the plurality of chambers.

The inlet port 103A receives conditioned air supplied by the variable-speed fan 118A and the dehydrating unit 122. The outlet port 103B is configured to facilitate the discharge of moisture-laden air away from the dehydrating cabinet 102.

In some embodiments, the inlet port 103A and the outlet port 103B cooperate to establish a directional airflow path across the food load, enabling uniform heat and mass transfer within the dehydrating cabinet 102.

In some embodiments, the dehydrating unit 122 is disposed within a lower or rear section of the dehydrating cabinet 102 and is configured to supply conditioned thermal energy to the chambers via ducted airflow channels. The dehydrating unit 122 ensures a uniform temperature distribution across the plurality of chambers 103 during dehydration.

In an embodiment, the display 202 of the food dehydration device 100 is operatively coupled to the microcontroller 116. The display 202 is configured to present real-time operational information, including chamber temperature, relative humidity levels, airflow status, dehydration progress, and system alerts.

In one embodiment, the microcontroller 116 is electrically connected to the display 202 to transmit processed sensor data and control status information. The display 202 may include a touch-sensitive interface that enables user input to set dehydration parameters, select operating modes, and initiate or terminate dehydration cycles. The integration of the display 202 with the microcontroller 116 enables local monitoring and control of the food dehydration device 100 and supports coordinated operation with the sensing array 110, the dehydrating unit 122, the airflow management unit 118, and the energy module 104.

The food dehydration device 100 further includes a switch 204 configured to selectively power the device on or off. The switch 204 is electrically coupled to the microcontroller 116 and is accessible from an exterior surface of the dehydrating cabinet 102. Actuation of the switch 204 enables the user to initiate or terminate electrical power delivery to the dehydrating unit 122, the airflow management unit 118, the sensing array 110, and the display 202.

In some embodiments, the switch 204 may include a safety-rated power cutoff configured to place the food dehydration device 100 into a safe shutdown state when actuated.

Figure 3:
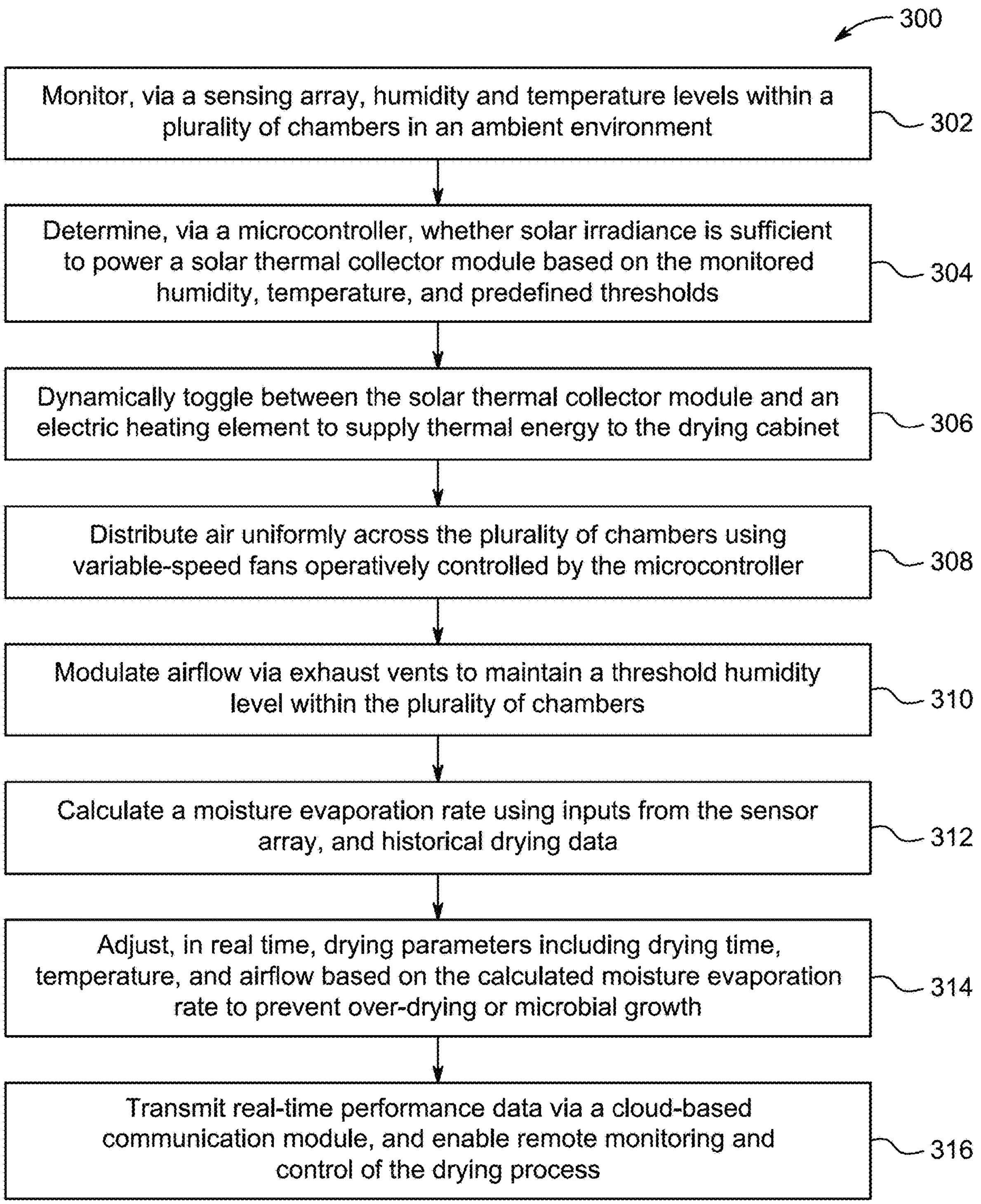
FIG. 3 is an exemplary flowchart of a method for drying food using the food dehydration device, according to certain embodiments.

Referring to FIG. 3, an exemplary flowchart of a method 300 for drying food using the food dehydration device 100 is illustrated, according to certain embodiments.

At step 302, the method 300 includes monitoring, via the sensing array 110, humidity and temperature levels within the plurality of chambers 103 in an ambient environment. The monitoring includes obtaining inlet relative humidity measurements from the first humidity sensor 110B, positioned near the inlet port 103A, and outlet relative humidity measurements from the second humidity sensor 110C, positioned near the outlet port 103B. Temperature measurements are obtained from the temperature sensor 114, which is disposed adjacent to the adjustable tray 103D within each chamber of the plurality of chambers 103. The sensing array 110 generates real-time sensor signals representative of airflow conditions prior to activation of the dehydrating unit 122.

At step 304, the method 300 includes determining, via the microcontroller 116, whether solar irradiance is sufficient to power a solar thermal collector module, based on monitored humidity and temperature and predefined thresholds. The microcontroller 116 evaluates monitored humidity and temperature levels obtained from the sensing array 110. The predefined thresholds may correspond to minimum chamber temperature requirements, target dehydration rates, or minimum solar energy contribution levels. Based on this evaluation, the microcontroller 116 determines whether the available solar irradiance is sufficient to provide supplemental or primary thermal energy through the solar thermal collector 106, or whether activation of the electric heating element 108 is required to maintain the desired dehydration conditions within the plurality of chambers 103.

At step 306, the method 300 includes dynamically toggling between the solar thermal collector module 106 and an electric heating element 108 to supply thermal energy to the drying cabinet 306. The microcontroller 116 selectively activates the solar thermal collector 106 when measured solar irradiance exceeds a predefined threshold, thereby providing supplemental or primary heating to the plurality of chambers 103. When solar irradiance is insufficient to maintain target chamber temperatures or generate desired dehydration rates, the microcontroller 116 activates the electric heating element 108 to provide additional thermal energy.

At step 308, the method 300 includes distributing air uniformly across the plurality of chambers 103 using the variable-speed fans 118A, which are operatively controlled by the microcontroller 116. The microcontroller 116 adjusts the rotational speed of the variable-speed fans 118A based on real-time feedback from the airflow sensor 110A and humidity sensors 112 to attain a uniform airflow velocity and pressure distribution within each chamber of the plurality of chambers 103. The microcontroller 116 further modulates the fan speed and coordinates with the exhaust vent 118B to optimize air circulation and attain energy-efficient dehydration.

At step 310, the method 300 includes modulating airflow via the exhaust vents 118B to maintain a threshold humidity level within the plurality of chambers 103. The microcontroller 116 receives real-time relative humidity data from the first humidity sensor 110B at the inlet port 103A and the second humidity sensor 110Cat the outlet port 103B of each chamber of the plurality of chambers 103. Based on this data, the microcontroller 116 actuates the actuators 120B associated with the exhaust vents 118B to adjust the vent aperture and regulate the exhaust flow path. The microcontroller 116 continuously updates the vent positions to dynamically balance airflow, compensate for variations in chamber load, and optimize energy-efficient operation of the food dehydration device 100.

At step 312, the method 300 includes calculating a moisture evaporation rate using inputs from the sensor array 110 and historical drying data. The sensing array 110 provides real-time measurements of relative humidity at the inlet port 103A and outlet port 103B, chamber temperature from the temperature sensor 114, and airflow velocity from the airflow sensor 110A. The microcontroller 116 processes these sensor inputs along with previously recorded dehydration profiles and empirical drying parameters to estimate the instantaneous moisture removal rate. Calculating the moisture evaporation rate enables the microcontroller 116 to dynamically adjust operating parameters of the dehydrating unit 122 and the airflow management unit 118, optimize dehydration efficiency, and maintain uniform moisture reduction across the plurality of chambers 103.

At step 314, the method 300 includes adjusting, in real time, drying parameters including drying time, temperature, and airflow based on the calculated moisture evaporation rate to prevent over-drying or microbial growth.

The microcontroller 116 receives the moisture evaporation rate computed from inputs provided by the sensing array 110, including relative humidity at the inlet port 103A and outlet port 103B, chamber temperature from the temperature sensor 114, and airflow velocity from the airflow sensor 110A.

The microcontroller 116 dynamically modulates the operation of the thermal unit 122A, the PEF unit 122B, the ultrasound-assisted dehydrating (UAD) unit 122C, the variable-speed fans 118A, and the exhaust vents 118B to maintain optimal dehydration conditions.

At step 316, the method 300 includes transmitting real-time performance data via the cloud-based communication module 120, and enables remote monitoring and control of the drying process. The transmitted performance data includes chamber temperature from the temperature sensor 114, relative humidity readings from the first humidity sensor 110B and the second humidity sensor 110C, airflow velocity from the airflow sensor 110A, moisture content of the food load, energy consumption of the thermal unit 122A, pulsed electric field (PEF) unit 122B, and ultrasound-assisted dehydrating (UAD) unit 122C, along with the status information of the variable-speed fans 118A and exhaust vents 118B.

The transmitted data enables remote monitoring and control of the dehydration process through a user-accessible dashboard. A user may view real-time chamber conditions, track dehydration progress, adjust setpoints for temperature, airflow, or dehydration time, and receive system alerts for threshold deviations or dehydration cycle completion.

Figure 4:
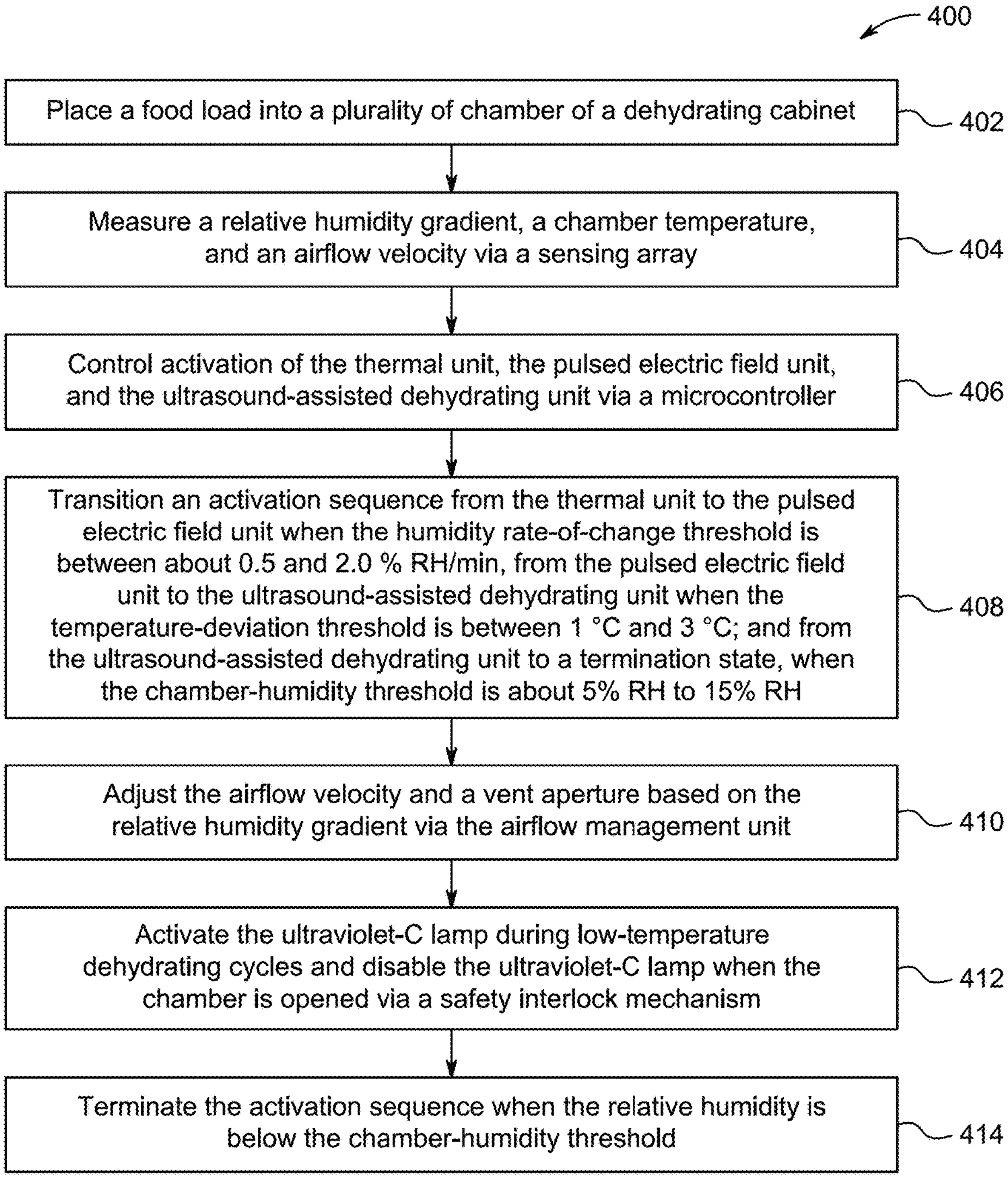
FIG. 4 is a flowchart of a method for dehydrating food using the safety interlock mechanism of the food dehydration device, according to certain embodiments.

Referring to FIG. 4, a flowchart of a method 400 for dehydrating food using the safety interlock mechanism 126 of the food dehydration device 100, according to certain embodiments.

At step 402, the method 400 includes placing a food load into the plurality of chambers 103 of a dehydrating cabinet 102. The plurality of chambers 103 includes the thermal unit 122A, the PEF unit 122B, the ultrasound-assisted dehydrating UAD unit, the airflow management unit 118, and the ultraviolet-C lamp 124.

The food load is positioned on the adjustable tray 103D within a selected chamber of the plurality of chambers 103 such that airflow, thermal energy, and auxiliary dehydration treatments are uniformly applied to the food load. Each chamber of the plurality of chambers 103 includes the thermal unit 122A, the pulsed electric field (PEF) unit 122B, the ultrasound-assisted dehydrating (UAD) unit 122C, the airflow management unit 118, and the ultraviolet-C (UV-C) lamp 124, which are arranged to operate in a coordinated manner during a dehydration cycle.

At step 404, the method 400 includes measuring a relative humidity gradient, a chamber temperature, and an airflow velocity via the sensing array 110. The relative humidity gradient is determined using the humidity sensors 110B, 110C, including the first humidity sensor 110B positioned proximate to the inlet port 103A and the second humidity sensor 110Cpositioned proximate to the outlet port 103B. The chamber temperature is measured by the temperature sensor 114 disposed adjacent to the adjustable tray 103D, and the airflow velocity is measured by the airflow sensor 110A disposed along a sidewall of each chamber of the plurality of chambers 103. The sensing array 110 generates real-time measurement data representative of environmental conditions within the chamber of the plurality of chambers 103, which is communicated to the microcontroller 116 for use in controlling dehydration parameters and sequencing operation of the dehydrating unit 122 and the airflow management unit 118.

The sensing array 110 includes the first humidity sensor 110B positioned about 10 to 30 mm, preferably 11 to 29 mm, preferably 12 to 28 mm, preferably 13 to 27 mm, preferably 14 to 26 mm, and preferably 15 to 25 mm, from an inlet port. The second humidity sensor 110Cis positioned about 10 to 30 mm, preferably 11 to 29 mm, preferably 12 to 28 mm, preferably 13 to 27 mm, preferably 14 to 26 mm, and preferably 15 to 25 mm, from the outlet port. The temperature sensor 114 is positioned about 5 to 30 mm, preferably 6 to 28 mm, preferably 7 to 26 mm, preferably 8 to 24 mm, preferably 9 to 22 mm, and preferably 10 to 20 mm, from a sidewall of the plurality of chambers 103. The airflow sensor 110A is disposed at an upper region of the sidewall of the plurality of chambers 103, about 20 to 50 mm, preferably 22 to 48 mm, preferably 24 to 46 mm, preferably 26 to 44 mm, preferably 28 to 42 mm, and preferably 30 to 40 mm, from the surface level of the adjustable tray.

Such placement enables accurate measurement of inlet and outlet relative humidity for determining a relative humidity gradient across each chamber of the plurality of chambers 103. This positioning allows the airflow sensor 110A to measure airflow velocity within the primary airflow path and minimize disturbance to airflow and food placement.

At step 406, the method 400 includes controlling activation of the thermal unit 122A, the PEF unit 122B, and the UAD unit 122C via the microcontroller 116 according to Equation (2):

$$S(t) = \begin{cases} \text{Thermal}, & \text{if } \frac{dH}{dt} < \alpha \\ PEF, & \text{if } \frac{dH}{dt} \geq \text{ and } \Delta T < \beta \\ UAD, & \text{if } H \leq \gamma \end{cases} \tag{2}$$

where:

S(t) represents a mode selection vector defining activation of the thermal unit 122A, the PEF unit 122B, and the UAD unit 122C, dH/dt is a humidity rate of change, ΔT is a temperature deviation, H is the relative humidity within the chamber of the plurality of chambers 103, α is a humidity rate-of-change threshold, β is a temperature-deviation threshold, and γ is a chamber-humidity threshold; and The microcontroller 116 is configured to activate the thermal unit 122A to raise the chamber temperature between 40° C. and 80° C. Transition and activation sequence includes from the thermal unit 122A to the PEF unit 122B when the humidity rate-of-change threshold is between about 0.5 and 2.0% RH/min, preferably 0.6 and 1.9% RH/min, preferably 0.7 and 1.8% RH/min, preferably 0.8 and 1.7% RH/min, preferably 0.9 and 1.6% RH/min, and preferably 1.0 and 1.5% RH/min. The activation sequence also includes the PEF unit transitioning to the UAD unit when the temperature deviation threshold is between 1° C. and 3° C. Transitioning the activation sequence further includes the UAD unit to a termination state, when the chamber-humidity threshold is about 5.0 to 15% RH, preferably 5.5 to 14.5% RH, preferably 6.0 to 14% RH, preferably 6.5 to 13.5% RH, preferably 7.0 to 13% RH, and preferably 7.5 to 12.5% RH.

The mode selection vector S(t) defines which dehydration mode is activated at a given time. When the rate of change of humidity $$\frac{dH}{dt}$$

is below the humidity rate-of-change threshold α, the microcontroller 116 activates the thermal unit 122A to promote convective moisture removal through controlled heating. When the rate of change of humidity $$\frac{dH}{dt}$$

equals or exceeds the threshold α and the temperature deviation ΔT remains below the temperature-deviation threshold β, the microcontroller 116 initiates activation of the pulsed electric field (PEF) unit 122B to enhance cellular permeability of the food load and accelerate moisture diffusion. When the relative humidity H within the chamber of the plurality of chambers 103 falls below the chamber-humidity threshold γ, the microcontroller 116 transitions activation to the ultrasound-assisted dehydrating (UAD) unit 122C to facilitate final-stage moisture removal via acoustic cavitation and microstreaming.

At step 408, the method 400 includes adjusting the airflow velocity and the vent aperture based on the relative humidity gradient via the airflow management unit 118. The airflow management unit 118 includes the variable-speed fan 118A and the exhaust vent 118B.

The microcontroller 116 receives inlet and outlet relative humidity measurements from the first humidity sensor 110B and the second humidity sensor 110Cof the sensing array 110 and determines the relative humidity gradient across each chamber of the plurality of chambers 103.

Based on the determined relative humidity gradient, the microcontroller 116 modulates the variable-speed fan 118A to adjust airflow velocity through the chamber and actuates the exhaust vent 118B to vary the vent aperture and regulate the exhaust flow path. When the relative humidity gradient exceeds a predefined threshold, the microcontroller 116 increases fan speed and opens the exhaust vent 118B to enhance moisture removal. Conversely, when the relative humidity gradient falls below the threshold, the microcontroller 116 reduces fan speed and partially closes the exhaust vent 118B to prevent over-drying and maintain stable chamber conditions. This coordinated control maintains uniform dehydration, optimizes airflow efficiency, and supports controlled moisture reduction across the plurality of chambers 103.

At step 410, the method 400 includes adjusting the airflow velocity and a vent aperture based on the relative humidity gradient via the airflow management unit 118. The airflow management unit 118 includes the variable-speed fan 118A and the exhaust vent 118B.

The microcontroller 116 processes relative humidity data obtained from the first humidity sensor 110B and the second humidity sensor 110Cof the sensing array 110 to compute the relative humidity gradient across each chamber of the plurality of chambers 103. Based on the computed gradient, the microcontroller 116 adjusts the rotational speed of the variable-speed fan 118A to regulate airflow velocity and actuates the exhaust vent 118B to adjust the vent aperture and control the exhaust flow path. Such coordinated adjustment enables maintenance of target humidity levels, promotes uniform moisture removal, and prevents localized over-drying or moisture retention within the plurality of chambers 103 during operation of the food dehydration device 100.

At step 412, the method 400 includes activating the UV C lamp 124 during low-temperature dehydrating cycles and disabling the UV C lamp 124 when the chamber of the plurality of chambers 103 is opened via the safety interlock mechanism 126.

The microcontroller 116 activates the UV-C lamp 124 when the chamber temperature is below a predefined threshold, thereby enabling microbial reduction and surface sterilization of the food load without requiring elevated thermal conditions.

The method 400 further includes disabling the UV-C lamp 124 when the chamber of the plurality of chambers 103 is opened via the safety interlock mechanism 126. In one or more embodiments, the safety interlock mechanism 126 detects an open-chamber condition and signals the microcontroller 116, which immediately deactivates the UV-C lamp 124 to prevent user exposure. This coordinated control ensures safe operation of the food dehydration device 100 while maintaining hygienic processing conditions during low-temperature dehydration cycles.

At step 414, the method 400 includes terminating the activation sequence when the relative humidity is below the chamber-humidity threshold. The microcontroller 116 continuously monitors relative humidity data from the humidity sensors 110B and 110C of the sensing array 110 and compares the measured relative humidity to the chamber-humidity threshold stored in memory associated with the microcontroller 116.

When the measured relative humidity is below the chamber-humidity threshold, the microcontroller 116 deactivates the thermal unit 122A, the pulsed electric field (PEF) unit 122B, and the ultrasound-assisted dehydrating (UAD) unit 122C, and reduces or stops airflow generated by the airflow management unit 118. Termination of the activation sequence signifies completion of the dehydration cycle and prevents over-drying of the food load. In one or more embodiments, the microcontroller 116 transitions the food dehydration device 100 to a standby state and generates a completion notification for transmission via the cloud-based communication module 120.

Figure 5:
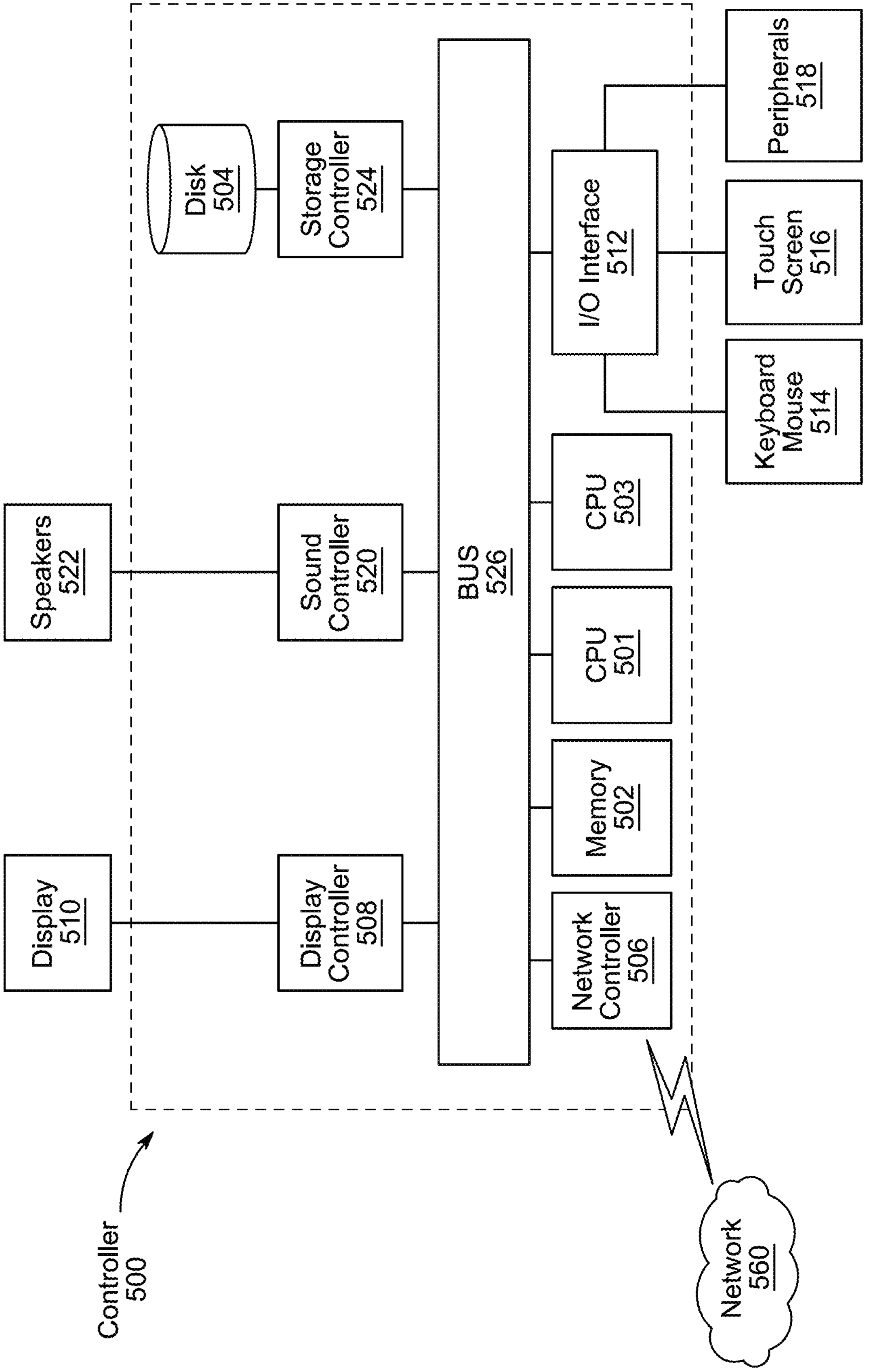
FIG. 5 is an illustration of a non-limiting example of details of computing hardware used in the microcontroller of the food dehydration device, according to certain embodiments.

In FIG. 5, a controller 500 is shown, embodying the microcontroller 116 of the food dehydration device 100 of the present disclosure. The controller 500 is a computing device coupled to a processor that includes a CPU 501, which performs the processes described above/below. The processed data and instructions may be stored in memory 502. These processes and instructions may also be stored on a storage medium disk 504, such as a hard drive (HDD) or portable storage medium, or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 501, 503 and an operating system such as Microsoft Windows 7, Microsoft Windows 10, Microsoft Windows 10, UNIX, Solaris, LINUX, Apple MAC-OS and other systems known to those skilled in the art.

The hardware elements for the computing device may be implemented using various circuitry elements, as known to those skilled in the art. For example, CPU 501 or CPU 503 may be a Xenon or Core processor from Intel of America, an Opteron processor from AMD of America, or another processor type recognized by one of ordinary skill in the art. Alternatively, the CPU 501, 503 may be implemented on an FPGA, ASIC, PLD, or using discrete logic circuits, as one of ordinary skill in the art may recognize. Furthermore, CPUs 501 and 503 may be implemented as multiple processors that cooperatively work in parallel to execute the instructions of the inventive processes described above.

The computing hardware in FIG. 5 also includes a network controller 506, such as an Intel Ethernet PRO network interface card from Intel Corporation of America, for interfacing with the network. As may be appreciated, the network may be a public network, such as the Internet, a private network, such as an LAN or WAN, or any combination thereof, and may also include PSTN or ISDN subnetworks. The network may also be wired, such as an Ethernet network, or may be wireless, such as a cellular network including EDGE, 3G, 4G, and 5G wireless cellular systems. The wireless network may also be Wi-Fi, Bluetooth, or any other known wireless communication technology.

The computing device further includes a display controller 508, such as a NVIDIA GeForce GTX or Quadro graphics adaptor from NVIDIA Corporation of America, for interfacing with display 510, such as a Hewlett Packard HPL2445w LCD monitor. A general-purpose I/O interface 512 interfaces with a keyboard and/or mouse 514, as well as a touch screen panel 516 on or separate from a display 510. General-purpose I/O interface also connects to a variety of peripherals 518 including printers and scanners, such as an OfficeJet or DeskJet from Hewlett-Packard.

A sound controller 520 is also provided in the computing device, such as Sound Blaster X-Fi Titanium from Creative, to interface with speakers/microphone 522, thereby providing sounds and/or music.

The general-purpose storage controller 524 connects the storage medium disk 504 to the communication bus 526, which may be an ISA, EISA, VESA, PCI, or similar, to interconnect the components of the computing device. A description of the general features and functionality of the display 510, keyboard and/or mouse 514, as well as the display controller 508, storage controller 524, network controller 506, sound controller 520, and general purpose I/O interface 512 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 6.

Figure 6:
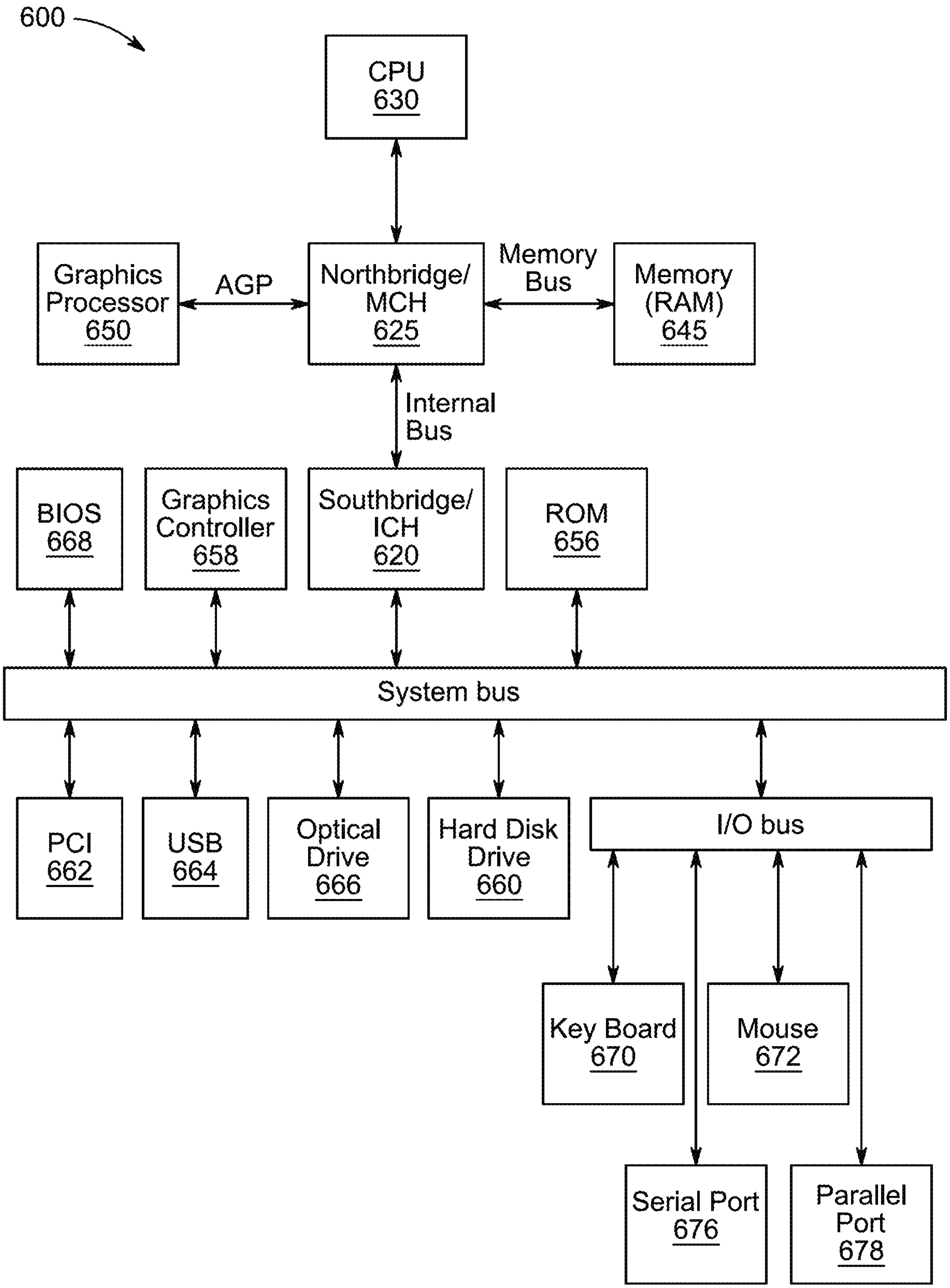
FIG. 6 is an exemplary schematic diagram of a data processing system used within the microcontroller of the food dehydration device, according to certain embodiments.

FIG. 6 shows a schematic diagram of a data processing system used within the microcontroller 116 of the food dehydration device 100, according to certain embodiments, for performing the functions of the exemplary embodiments. The data processing system is an example of a computer in which code or instructions implementing the processes of the illustrative embodiments may be located.

In FIG. 6, data processing system 600 employs a hub architecture including a north bridge and memory controller hub (NB/MCH) 625 and a south bridge and input/output (I/O) controller hub (SB/ICH) 620. The central processing unit (CPU) 630 is connected to NB/MCH 625. The NB/MCH 625 also connects to the memory 645 via a memory bus, and connects to the graphics processor 650 via an accelerated graphics port (AGP). The NB/MCH 625 also connects to the SB/ICH 620 via an internal bus (e.g., a unified media interface or a direct media interface). The CPU Processing unit 630 may contain one or more processors and may even be implemented using one or more heterogeneous processor systems.

Figure 7:
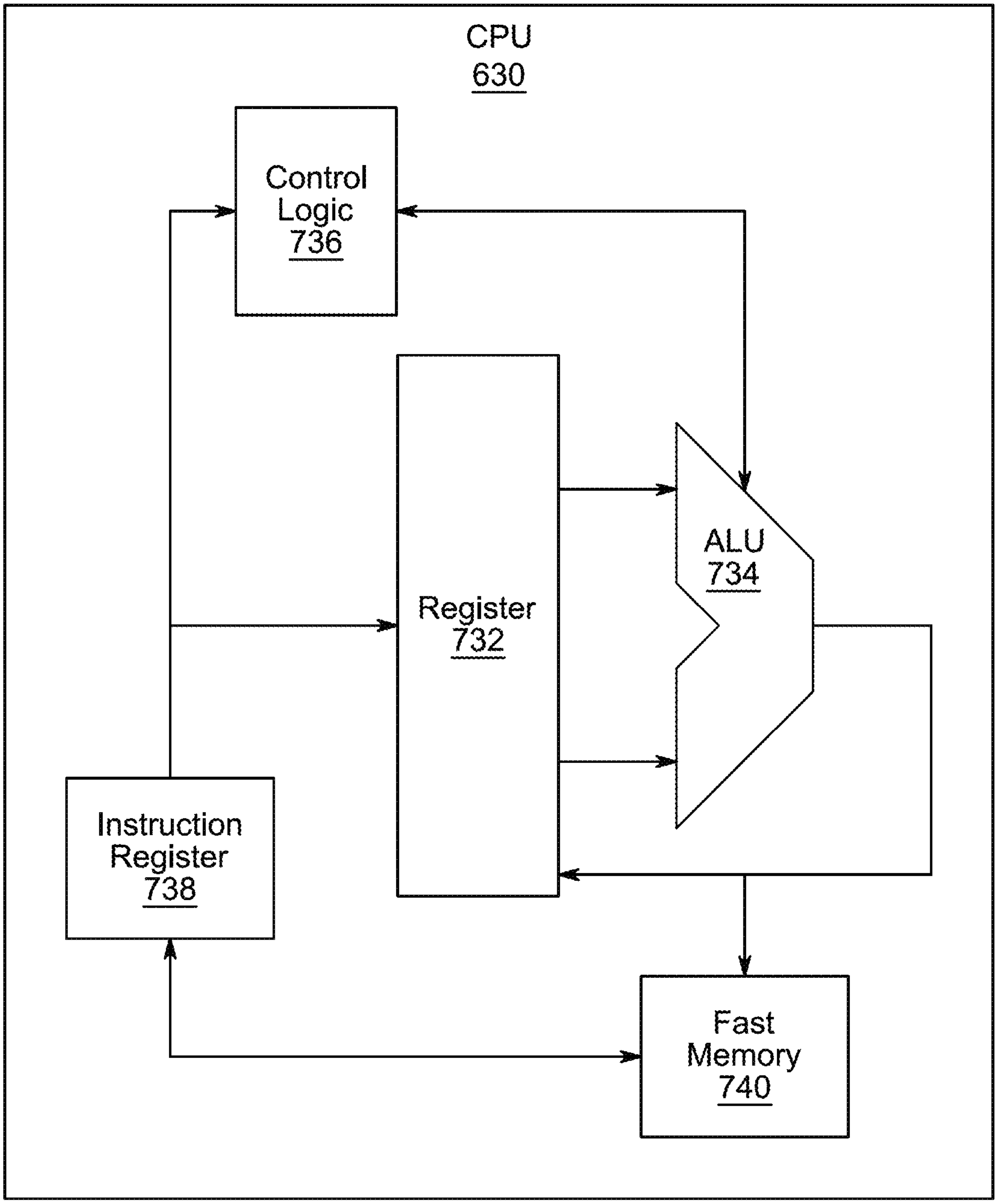
FIG. 7 is an exemplary schematic diagram of a processor of the food dehydration device, according to certain embodiments.

For example, FIG. 7 shows one implementation of CPU 630. In one implementation, the instruction register 738 retrieves instructions from the fast memory 740. At least part of these instructions are fetched from the instruction register 738 by the control logic 736 and interpreted according to the instruction set architecture of the CPU 630. Part of the instructions may also be directed to the register 732. In one implementation, the instructions are decoded according to a hardwired method, and in another implementation, the instructions are decoded according to a microprogram that translates instructions into sets of CPU configuration signals that are applied sequentially over multiple clock pulses. After fetching and decoding the instructions, the instructions are executed using the arithmetic logic unit (ALU) 734 that loads values from the register 732 and performs logical and mathematical operations on the loaded values according to the instructions. The results from these operations may be fed back into the register and/or stored in the fast memory 740. According to certain implementations, the instruction set architecture of the CPU 630 may use a reduced instruction set architecture, a complex instruction set architecture, a vector processor architecture, and a very large instruction word architecture.

Furthermore, the CPU 630 may be based on the Von Neumann model or the Harvard model. The CPU 630 may be a digital signal processor, an FPGA, an ASIC, a PLA, a PLD, or a CPLD. Further, the CPU 630 may be an x86 processor by Intel or AMD; an ARM processor; a Power architecture processor by, e.g., IBM; a SPARC architecture processor by Sun Microsystems or Oracle; or another known CPU architecture.

Referring again to FIG. 6, the data processing system 600 may include the SB/ICH 620 is coupled through a system bus to an I/O Bus, a read-only memory (ROM) 656, a universal serial bus (USB) port 664, a flash binary input/output system (BIOS) 668, and a graphics controller 658. PCI/PCIe devices may also be coupled to SB/ICH 688 through a PCI bus 662.

The PCI devices may include, for example, Ethernet adapters, add-in cards, and PC cards for notebook computers. The Hard disk drive 660 and CD-ROM 666 may use, for example, an Integrated Drive Electronics (IDE) or Serial Advanced Technology Attachment (SATA) interface. In one implementation, the I/O bus may include a super I/O (SIO) device.

Furthermore, the hard disk drive (HDD) 660 and optical drive 666 may be coupled to the SB/ICH 620 via a system bus. In one implementation, a keyboard 670, a mouse 672, a parallel port 678, and a serial port 676 may be connected to the system bus through the I/O bus. Other peripherals and devices that may be connected to the SB/ICH 620 include a mass storage controller (SATA or PATA), an Ethernet port, an ISA bus, an LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes in battery sizing and chemistry or based on the requirements of the intended backup load to be powered.

Figure 8:
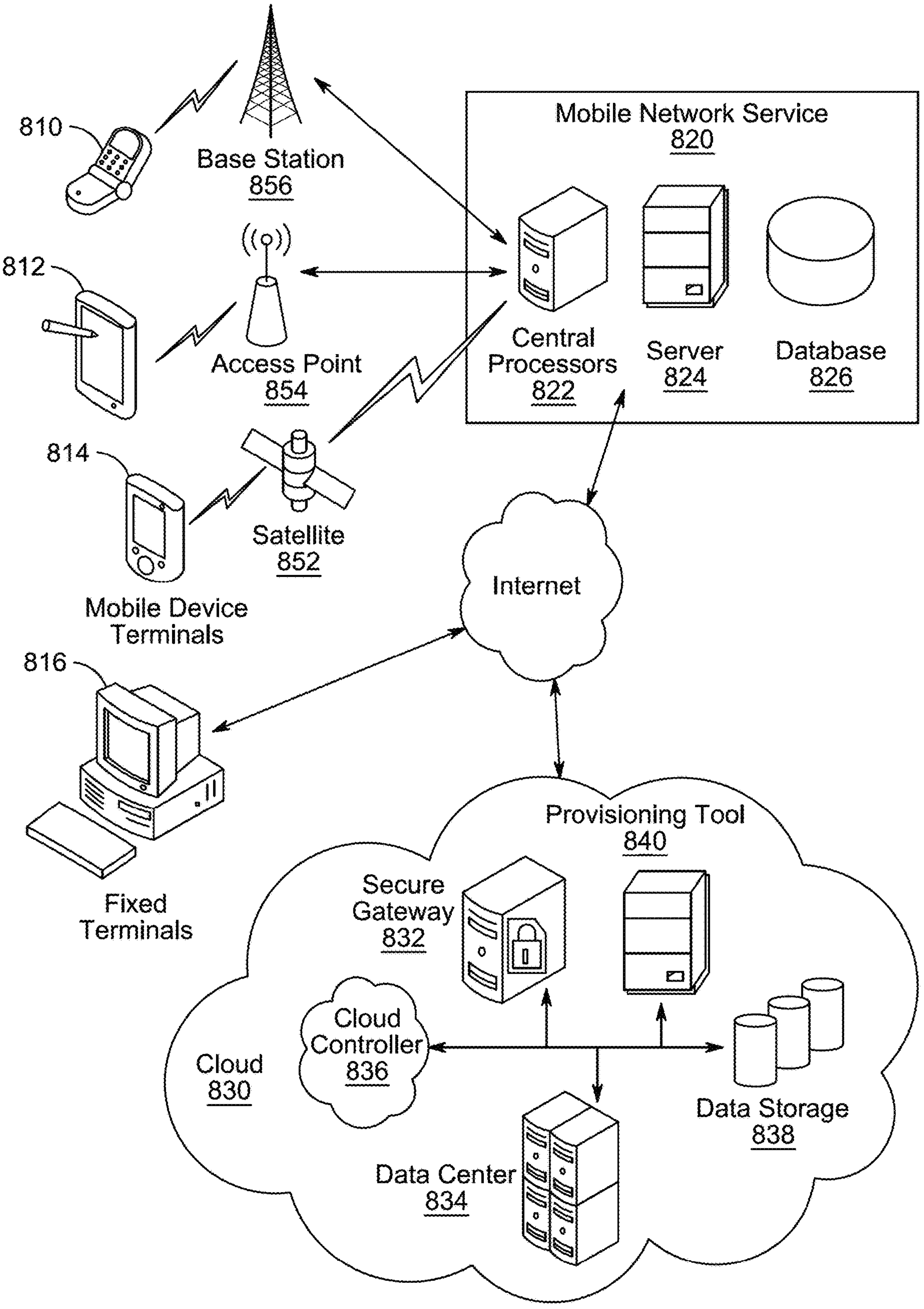
FIG. 8 is an illustration of a non-limiting example of distributed components that may share processing with the microcontroller of the food dehydration device, according to certain embodiments.

The functions and features described herein may also be executed by various distributed components of a system. For example, one or more processors may execute these system functions, with the processors distributed across multiple components that communicate over a network. The distributed components may include one or more client and server machines, such as cloud 830 including a cloud controller 836, a secure gateway 832, a data center 834, data storage 838 and a provisioning tool 840, and mobile network services 820 including central processors 822, a server 824 and a database 826, which may share processing, as shown by FIG. 8, in addition to various human interface and communication devices (e.g., display monitors 816, smart phones 810, tablets 812, personal digital assistants (PDAs) 814). The network may be a private network, such as a LAN, satellite 852, or WAN 854, or a public network, such as the Internet. Input to the system may be received directly from users and remotely in real time or as a batch process. Additionally, some implementations may be performed on modules or hardware not identical to those described. Accordingly, other implementations are within the scope that may be claimed.

The above-described hardware description is a non-limiting example of a corresponding structure for performing the functionality described herein.

Numerous modifications and variations of the present disclosure are possible in light of the above teachings. It is therefore to be understood that within the scope of the appended claims, the invention may be practiced otherwise than as specifically described herein.

The invention claimed is:

1. A food dehydration device comprising:
- a dehydrating cabinet comprising a plurality of chambers, wherein each chamber comprises an inlet port, an outlet port, a removable partition, and an adjustable tray,
- wherein the chambers are thermally isolated from one another by the removable partition selected from the group consisting of:
  - an aerogel-based insulation panel,
  - a vacuum-insulated panel (VIP),
  - a ceramic-fiber insulation panel, and
  - a silica-based microporous insulation panel;
- a sensing array disposed within each chamber, wherein each sensing array comprises:
  - a humidity sensor positioned at the inlet port, the outlet port, and configured to measure a relative humidity gradient;
  - a temperature sensor positioned at the tray and configured to detect a chamber temperature; and
  - an airflow sensor positioned at an upper region of a sidewall of the chambers and configured to measure an airflow velocity;
- a dehydrating unit disposed in the chambers, comprising:
  - a thermal unit configured to deliver heat energy;
  - a pulsed electric field (PEF) unit configured to deliver high-voltage pulses; and
  - an ultrasound-assisted dehydrating (UAD) unit configured to generate acoustic waves;
- an ultraviolet-C (UV-C) lamp disposed in the chambers and configured to activate during low-temperature dehydrating cycles,
- a safety interlock mechanism configured to deactivate the UV-C lamp, the PEF unit, and the UAD unit when a corresponding chamber is open,
- an airflow management unit comprising:
  - a variable-speed fan disposed at the inlet port and the outlet port configured to drive air through the chambers; and
  - an exhaust vent disposed at the outlet port comprising actuators configured to regulate an exhaust flow path;
- wherein the airflow management unit is configured to:
  - modulate an airflow based on the relative humidity gradient between the inlet port and the outlet port, and
  - adjust a fan speed and a vent aperture to maintain an uniform dehydrating condition across the chambers;
- an energy module disposed at a surface of the cabinet, wherein the energy module comprises a solar thermal collector and an electric heating element,
- a microcontroller operatively coupled to the energy module, the sensing array, the UV-C lamp, the dehydrating unit, and the airflow management unit,
- wherein the microcontroller is configured to:
  - compute a power output to the dehydrating unit and the airflow management unit,
  - calculate a moisture content of a food load, and
  - dynamically adjust the relative humidity gradient, the chamber temperature, and the relative humidity within the chambers; and
- a cloud-based communication module configured to:
  - transmit performance data and system alerts to a remote display interface, and
  - transmit an external input to the microcontroller.

2. The device of claim 1, wherein the dehydrating cabinet is constructed from a corrosion-resistant material selected from the group consisting of stainless steel, aluminum alloy, and a polymer-metal composition;
- wherein the dehydrating cabinet comprises one or more walls having a thickness between about 1.0 and 4.0 mm;
- wherein the dehydrating cabinet has an overall internal volume between about 50 and 500 liters; and
- wherein each chamber within the dehydrating cabinet has:
  - a width between about 150 and 600 mm,
  - a depth between about 200 and 800 mm, and
  - a height between about 150 and 700 mm.

3. The device of claim 1, wherein the sensing array comprises:
- a first humidity sensor positioned about 5 to 20 mm from the inlet port;
- a second humidity sensor positioned about 5 to 20 mm from the outlet port;
- the temperature sensor disposed at the adjustable tray about 5 to 30 mm from the sidewall of the chambers;
- the airflow sensor disposed at the sidewall of the chambers, about 20 to 50 mm from a surface level of the tray; and
- wherein each sensor is encapsulated in a polymer coating selected from the group consisting of a parylene-C conformal coating, a silicone-based encapsulant, and a fluoropolymer coating.

4. The device of claim 1, wherein the humidity sensor comprises a polymer-film humidity sensor selected from the group consisting of:
- a polyimide-based capacitive humidity sensor,
- a polyethylene-terephthalate (PET)-based capacitive humidity sensor,
- a polyvinyl-alcohol (PVA)-based capacitive humidity sensor,
- a cellulose-acetate-based capacitive humidity sensor, and
- a fluoropolymer-based capacitive humidity sensor; and
- wherein the humidity sensor has a sensing area of about 4 to 25 $mm^2$.

5. The device of claim 1, wherein the temperature sensor comprises a thin-film resistive temperature detector (RTD) selected from the group consisting of:
- a platinum thin-film RTD,
- a nickel thin-film RTD,
- a copper thin-film RTD,
- a graphene-based thermoresistive temperature sensor, and
- a MXene-based thermoresistive temperature sensor; and wherein the temperature sensor has a sensing area between 3 and 20 $mm^2$.

6. The device of claim 1, wherein the airflow sensor is selected from the group consisting of: a thermal-anemometric airflow sensor, a MEMS-based airflow sensor, a hot-wire airflow sensor, a piezoresistive differential-pressure airflow sensor, and an ultrasonic time-of-flight airflow sensor; and wherein the airflow sensor has a sensing area between about 3 and 20 $mm^2$.

7. The device of claim 1, wherein the thermal unit comprises a convective heating element selected from the group consisting of an electrical resistance heating coil, a ceramic heating element, a finned tubular heater, and a radiant-convective hybrid heater; and wherein the thermal unit is configured to:

deliver the heat energy to the chambers via a forced airflow generated by the variable-speed fan at the airflow velocity of about 0.5 to 5.0 m/s, operate at the power output between 300 and 1500 W, adjust a thermal response time sufficient to raise the chamber temperature from 25° C. to 60° C. within about 2 to 6 minutes, and maintain the chamber temperature at about 40° C. to 80° C. during dehydration.

8. The device of claim 1, wherein the PEF unit comprises parallel-plate electrodes spaced between 5 mm and 25 mm apart, and operates at a repetition rate between 10 Hz and 500 Hz; and wherein the PEF unit comprises a high-voltage pulse generator selected from the group consisting of:

a capacitor-discharge pulse generator, a Marx-bank pulse generator, and a solid-state insulated-gate bipolar transistor (IGBT) pulse generator; and wherein the PEF unit is configured to generate the high-voltage pulses having a field strength between 0.5 and 5 kV/cm, and a pulse width between 1 and 50 μs.

9. The device of claim 1, wherein the UAD unit comprises at least one ultrasonic transducer disposed on the sidewall of the chambers;

wherein the ultrasonic transducer is selected from the group consisting of:

a piezoelectric ceramic transducer, a piezoelectric composite transducer, a magnetostrictive transducer, and a thin-film MEMS ultrasonic transducer; and wherein the ultrasonic transducer operates at about 20 to 60 kHz and at a duty cycle of about 20 to 80%.

10. The device of claim 1, wherein the UV-C lamp comprises at least one emitter selected from the group consisting of:

a low-pressure mercury vapor emitter, a pulsed-xenon excimer emitter, a krypton-chloride excimer emitter, a UV-C light-emitting diode (LED) emitter, and a plasma discharge emitter; and wherein the UV-C lamp emits radiation between 200 and 280 nm and has an irradiance output between 0.5 and 3.0 $mW/cm^2$.

11. The device of claim 1, wherein the safety interlock mechanism comprises at least one selected from the group consisting of a magnetic reed switch, a mechanical micro-switch, an optical proximity sensor, and a Hall-effect sensor.

12. The device of claim 1, wherein the variable-speed fan comprises a brushless DC (BLDC) motor actuator selected from the group consisting of:

a sensorless BLDC actuator, a Hall-sensor-based BLDC actuator, a PWM-driven BLDC actuator, and a closed-loop BLDC actuator; and wherein the variable-speed fan is configured to:

generate the airflow velocity between 0.5 m/s and 5.0 m/s, and maintain a static pressure between 20 and 120 Pa.

13. The device of claim 1, wherein the exhaust vent comprises a stepper-motor-driven actuator selected from the group consisting of:

a bipolar stepper motor, a unipolar stepper motor, a micro-stepping stepper motor, a permanent-magnet stepper actuator, and a variable-reluctance stepper actuator; and wherein the exhaust vent is configured to:

modulate the vent aperture between 5% and 95% open, regulate exhaust flow rate about 0.1 to 1.5 $m^3$/min, and maintain a pressure-balanced airflow across the chambers.

14. The device of claim 1, wherein the solar thermal collector is selected from the group consisting of a flat-plate solar thermal collector, an evacuated-tube solar collector, and a compound parabolic concentrator;

wherein the solar thermal collector is configured to provide supplemental heating when solar irradiance exceeds 300 $W/m^2$; and wherein the solar thermal collector is thermally coupled to the dehydrating cabinet to heat the chambers through a convective heat-exchange interface comprising at least one of:

a direct air-loop coupling; and a closed-loop thermal fluid circuit, wherein the thermal fluid circuit operates at a flow rate of about 0.2 to 1.5 L/min.

15. The device of claim 1, wherein the microcontroller comprises a multivariable proportional-integral-derivative (PID) control model configured to compute the power output u(t) according to a mathematical expression (1):

$$u(t) = K_p e(t) + K_i \int_0^t e(\tau)d\tau + K_d \frac{de(t)}{dt} \tag{1}$$

where:

$$e(t) = \begin{bmatrix} e_H(t) \\ e_T(t) \end{bmatrix}$$

represents humidity and temperature error vectors, $$u(t) = \begin{bmatrix} u_F(t) \\ u_V(t) \end{bmatrix}$$

represents the power output applied to the thermal unit and the airflow management unit, $K_p$ is a proportional gain matrix of about 0.5 and 3.0, $K_i$ is an integral gain matrix of about 0.01 $s^{-1}$ to 0.50 $s^{-1}$, and $K_d$ is a derivative gain matrix of about 0.001 s to 0.10 s.

16. The device of claim 1, wherein the microcontroller is configured to control activation of the thermal unit, the PEF unit, and the UAD unit according to an activation sequence defined by Equation (2)

$$S(t) = \begin{cases} \text{Thermal}, & \text{if } \frac{dH}{dt} < \alpha \\ PEF, & \text{if } \frac{dH}{dt} \geq \alpha \text{ and } \Delta T < \beta \\ UAD, & \text{if } H \leq \gamma \end{cases} \quad (2)$$

where:

S(t) represents a mode-selection vector defining activation of the thermal unit, the PEF unit, and the UAD unit, $$\frac{dH}{dt}$$

is a humidity rate of change,

ΔT is a temperature deviation,

H is the relative humidity within the chambers,

α is a humidity rate-of-change threshold between about 0.5 and 2.0% RH/min,

β is a temperature-deviation threshold between about 1° C. and 3° C., and

γ is a chamber-humidity threshold between about 5% RH and 20% RH; and wherein the microcontroller is configured to transition the activation sequence comprising:

from the thermal unit to the PEF unit when the humidity rate of change exceeds the humidity rate-of-change threshold;

from the PEF unit to the UAD unit when the temperature deviation is below the temperature-deviation threshold; and from the UAD unit to a termination state, when the relative humidity is below the chamber-humidity threshold.

17. The device of claim 16, wherein the microcontroller is further configured to apply a multi-condition gating to the activation sequence, comprising:

initiating the thermal unit to raise the chamber temperature between 40° C. and 80° C., initiating the PEF unit when:

the humidity rate of change exceeds a humidity-rate-of-change threshold between 0.5 and 2.0% RH/min, and the chamber temperature is between 35° C. and 50° C.;

initiating the UAD unit when:

the temperature deviation remains within the temperature-deviation threshold between 1° C. and 3° C., and the relative humidity gradient between the inlet and outlet ports is about 3% RH to 15% RH;

maintaining the UAD unit while:

the relative humidity decreases at a rate between 0.2 and 1.0% RH/min, and the airflow velocity remains between 0.5 and 3.0 m/s; and terminating the activation sequence when either:

the relative humidity is below a termination threshold between 5% RH and 15% RH, or the humidity rate of change is below 0.1% RH/min for a duration of 5 to 20 seconds.

18. The device of claim 16, wherein the microcontroller is further configured to modify the activation sequence according to a load-normalized energy $E_m(t)$ defined by Equation (3):

$$E_m(t) = \frac{P_{thermal}(t) + P_{PBF}(t) + P_{UAD}(t)}{M_{load}} \quad (3)$$

where:

$P_{thermal}(t)$, $P_{PEF}(t)$, and $P_{UAD}(t)$ represent an energy consumption of the thermal unit, the PEF unit, and the UAD unit, respectively, and $M_{load}$ represents a mass of the food load within the chambers; and wherein the microcontroller is configured to:

attenuate the high-voltage pulses from the PEF unit when the load-normalized energy exceeds about 5 W/kg to 20 W/kg; and limit the duty cycle from the UAD unit to about 40 to 60% when the load-normalized energy exceeds about 8 to 25 W/kg.

19. The device of claim 1, wherein the microcontroller is configured to compute the moisture content M(t) of the food load according to Equation (4):

$$M(t) = k_v \cdot v_{air}(t) \cdot [RH_{in}(t) - RH_{out}(t)] \cdot f(T_{ch}(t)) \quad (4)$$

where:

$v_{air}(t)$ is the airflow velocity, $RH_{in}(t)$ and $RH_{out}(t)$ are inlet and outlet relative humidities, $T_{ch}(t)$ is the chamber temperature, $k_v$ is a calibration coefficient between 0.001 and 0.050 kg $m^{-3} \cdot s^{-1}$, $f(T_{ch}(t))$ is a temperature-dependent correction factor; and wherein the microcontroller is configured to update the moisture content M (t) at intervals between 0.5 and 5 seconds.

20. A method for dehydrating food using a food dehydration device comprising:

placing a food load into a chamber of a dehydrating cabinet, wherein the chamber comprises a thermal unit, a pulsed electric field (PEF) unit, an ultrasound-assisted dehydrating (UAD) unit, an airflow management unit, and an ultraviolet-C (UV-C) lamp;

measuring a relative humidity gradient, a chamber temperature, and an airflow velocity via a sensing array, wherein the sensing array comprises:

a first humidity sensor positioned about 10 to 30 mm from an inlet port, a second humidity sensor positioned about 10 to 30 mm from an outlet port, a temperature sensor positioned about 5 to 30 mm from a sidewall of the chambers, and an airflow sensor disposed at an upper region of the sidewall of the chambers, about 20 to 50 mm from a surface level of an adjustable tray;

controlling activation of the thermal unit, the PEF unit, and the UAD unit via a microcontroller according to Equation (2):

$$S(t) = \begin{cases} \text{Thermal}, & \text{if } \frac{dH}{dt} < \alpha \\ PEF, & \text{if } \frac{dH}{dt} \geq \alpha \text{ and } \Delta T < \beta \\ UAD, & \text{if } H \leq \gamma \end{cases} \quad (2)$$

where:

S(t) represents a mode-selection vector defining activation of the thermal unit, the PEF unit, and the UAD unit, $$\frac{dH}{dt}$$

is a humidity rate of change,

ΔT is a temperature deviation,

H is the relative humidity within the chamber,

α is a humidity rate-of-change threshold,

β is a temperature-deviation threshold, and

γ is a chamber-humidity threshold; and wherein the microcontroller is configured to:

activate the thermal unit to raise the chamber temperature between 40° C. and 80° C.; and transition an activation sequence comprising:

from the thermal unit to the PEF unit when the humidity rate-of-change threshold is between about 0.5 and 2.0% RH/min;

from the PEF unit to the UAD unit when the temperature-deviation threshold is between 1° C. and 3° C.; and from the UAD unit to a termination state, when the chamber-humidity threshold is about 5 to 15% RH;

adjusting the airflow velocity and a vent aperture based on the relative humidity gradient via the airflow management unit, wherein the airflow management unit comprises a variable-speed fan and an exhaust vent;

activating the UV-C lamp during low-temperature dehydrating cycles and disabling the UV-C lamp when the chamber is opened via a safety interlock mechanism, and terminating the activation sequence when the relative humidity is below the chamber-humidity threshold.

* * * * *